(12) United States Patent
Griswold-Prenner et al.

(10) Patent No.: US 12,071,649 B1
(45) Date of Patent: Aug. 27, 2024

(54) IDENTIFICATION OF MODULATORS OF NITRATION AND THERAPEUTIC USES THEREOF

(71) Applicant: Nitrase Therapeutics, Inc., Brisbane, CA (US)

(72) Inventors: Irene Griswold-Prenner, Jackson, WY (US); Sami Hussain, San Francisco, CA (US); Vu Cao Dang, San Mateo, CA (US)

(73) Assignee: Nitrase Therapeutics, Inc., Brisbane, CA (US)

( * ) Notice: Subject to any disclaimer, the term of this patent is extended or adjusted under 35 U.S.C. 154(b) by 198 days.

(21) Appl. No.: 16/207,796

(22) Filed: Dec. 3, 2018

Related U.S. Application Data

(60) Provisional application No. 62/593,941, filed on Dec. 3, 2017.

(51) Int. Cl.
| | | |
|---|---|---|
| *G01N 33/53* | (2006.01) | |
| *C07K 16/18* | (2006.01) | |
| *C12Q 1/25* | (2006.01) | |
| *G01N 33/68* | (2006.01) | |

(52) U.S. Cl.
CPC .............. *C12Q 1/25* (2013.01); *C07K 16/18* (2013.01); *G01N 33/6896* (2013.01); *G01N 2440/00* (2013.01); *G01N 2500/20* (2013.01); *G01N 2800/2835* (2013.01)

(58) Field of Classification Search
None
See application file for complete search history.

(56) References Cited

U.S. PATENT DOCUMENTS

| | | |
|---|---|---|
| 8,710,051 B2 | 4/2014 | Wischik et al. |
| 2012/0264783 A1 | 10/2012 | Went et al. |

FOREIGN PATENT DOCUMENTS

| | | |
|---|---|---|
| ES | 2481517 A2 | 7/2014 |
| WO | WO-2023/077122 A1 | 5/2023 |

OTHER PUBLICATIONS

Liu et al., A novel molecular mechanism for nitrated a-synuclein-induced cell death, Journal of Molecular Cell Biology, 2011, 3, pp. 239-249. (Year: 2011).*
Schildknecht et al., Oxidative and nitrative alpha-synuclein modifications and proteostatic stress: implications for disease mechanisms and interventions in synucleinopathies, Journal of Neurochemistry, 125, 2013, 4, S 491-511. (Year: 2013).*
Daiber et al., Nitration and inactivation of cytochrome P450 by peroxynitrite stopped-flow measurement prove ferryl intermediates, Eur. J. Biochem. 267, 2000, pp. 6729-6739. (Year: 2000).*
Chavarría et al., "Oxidation and nitration of alpha-synuclein and their implications in neurodegenerative diseases," Arch Biochem Biophys. 533(1-2): 25-32 (2013).
Berge et al., "Pharmaceutical salts," J Pharm Sci. 66(1):1-19 (1977).
Guillory, "Handbook of Pharmaceutical Salts: Properties, Selection, and Use. Edited by P. Heinrich Stahl and Camile G. Wermuth. VHCA, Verlag Helvetica Chimica Acta, Zürich, Switzerland, and Wiley-VCH, Weinheim, Germany. 2002. vix + 374 pp. 17.5 × 24.5 cm. ISBN 3-906390-26-8. $130.00," Book Reviews, Journal of Medicinal Chemistry. 46(7):1277 (2003).
Application for International Application No. PCT/US2022/078980, filed Oct. 31, 2022 (46 pages).
Fernández et al., "May the evaluation of nitrosative stress through selective increase of 3-nitrotyrosine proteins other than nitroalbumin and dominant tyrosine-125/136 nitrosylation of serum a-synuclein serve for diagnosis of sporadic Parkinson's disease?," Antioxid Redox Signal. 19(9):912-8 (Sep. 20, 2013).
Jennings et al., "Imaging prodromal Parkinson disease: the Parkinson Associated Risk Syndrome Study," Neurology 83(19): 1739-46 (Nov. 4, 2014).
Miranda et al., "Posttranslational modifications of blood-derived alpha-synuclein as biochemical markers for Parkinson's disease," Sci Rep. 7(1):13713, pp. 1-11 (Oct. 20, 2017).

* cited by examiner

*Primary Examiner* — Gary Counts
(74) *Attorney, Agent, or Firm* — Clark & Elbing LLP

(57) ABSTRACT

The present invention features methods for identifying treatments for neurodegenerative diseases, e.g., Parkinson's disease. Described are purification methods for synuclein nitration enzyme and screening methods for identifying agents that inhibit synuclein nitration enzyme activity.

10 Claims, 23 Drawing Sheets
Specification includes a Sequence Listing.

IDENTIFICATION OF MODULATORS OF NITRATION AND THERAPEUTIC USES THEREOF

BACKGROUND OF THE INVENTION

Nitration of proteins has been linked to various disease conditions through inducement of agglomeration of proteins. Nitration is known to play a role in cardiovascular disease, oncology, and stroke. Nitration has also been shown to play a role in neurodegenerative diseases, e.g., Alzheimer's disease (AD), Parkinson's disease (PD), amyotrophic lateral sclerosis (ALS), and Huntington's disease. The relevance of nitration has been demonstrated for α-synuclein structure and tyrosine hydroxylase activity in aging and diseases, e.g., cardiovascular and neurodegenerative diseases, e.g., PD, AD, cancer, stroke, and heart attack.

Parkinson's disease is the second most common neurodegenerative disease, affecting one million people in the United States alone. The disease is characterized by a dramatic loss of dopaminergic neurons in the Substantia Nigra with up to 80% of these neurons having degenerated by the time of clinical manifestations. Death of these neurons causes tremor, bradykinesia, rigidity, and postural instability. There is no effective intervention to slow, halt, or reverse disease progression. A hallmark of Parkinson's disease (PD) pathology is an intracellular accumulation of α-synuclein aggregates resulting in Lewy Bodies and Lewy Neurites. It has been hypothesized that these α-synuclein aggregates, in some form, are responsible for causing PD. Another prominent characteristic of PD and of many other neurodegenerative diseases, including Alzheimer's disease, Progressive Supranuclear Palsy (PSP), and Frontotemporal Dementia (FTD), is the age-dependent nature of these disorders. This suggests that aging provides an additive factor in the development of neurodegenerative diseases.

The present disclosure relates to methods useful for the identification of treatments for neurodegenerative disease, e.g., Parkinson's disease.

SUMMARY OF THE INVENTION

α-Synuclein (alpha-synuclein) has been shown to be nitrated in the inclusions present in PD, dementia with Lewy Bodies (DLB), Lewy body variant of AD, and Multiple-System Atrophy (MSA). Several studies have suggested that the insolubility of α-synuclein may be a result of nitration, since nitrated α-synuclein is present in the insoluble (not soluble) fraction of homogenates from PD brains. α-Synuclein nitration also induces oligomerization and β-pleated (beta-pleated) sheet formation in a nucleation-dependent manner. Furthermore, nitration of α-synuclein results in its removal from lipid vesicles and increases its half-life due to decreased ability of the proteasome to degrade it. Each of these factors contributes to α-synuclein accumulation and aggregation.

A role for the adverse effects of α-synuclein nitration and dityrosine crosslinking was also shown in two independent in vivo models of PD. One model mimics α-synuclein dityrosine crosslinking in an α-synuclein transgenic mouse model in which tyrosine 39 is replaced with cysteine facilitating inter-synuclein disulfide crosslinking. In a second model, nitrated α-synuclein was microinjected into dopaminergic neurons in the rat ventral mesencephalon. In both in vivo PD models, α-synuclein aggregation and either tyrosine hydroxylase positive cell loss and motor deficits or cognitive and motoric dysfunction were observed. The data suggest a role of α-synuclein nitration in mediating disease pathology and dysfunction in neurodegenerative disease, such as PD. Finding a mechanism to specifically inhibit this nitration event could be highly advantageous for the drug discovery efforts for treatment of neurodegenerative disease, such as PD, and its symptoms.

In the past, it was believed that this nitration was the result of chemical transformation via free radicals, e.g., nitric oxide. In fact, the dogma in the oxidative stress field still remains that protein nitration is strictly a chemical reaction due to the high level of reactivity and lability of oxygen free radicals. Recent studies have shown that familial ALS (fALS) mutations in SOD1 (Cu,Zn-superoxide dismutase-1) cause the mutated SOD1 to catalyze the nitration of its protein substrates. The enzyme activity of fALS mutant SOD1 is weak but demonstrates enzyme-catalyzed protein nitration.

The exquisite selectivity of protein nitration in tissues from PD patients and animal models also suggests a directed and specific protein nitration and does not support the concept of chemical reaction mediated nitration alone. To the best of our knowledge, prior to the present disclosure, no one has considered that there may be a biological basis for nitration of α-synuclein.

Herein, it has been demonstrated that nitration of α-synuclein is enzyme-dependent and can be inhibited by compounds, e.g., small molecules, that slow or block α-synuclein-dependent neurodegeneration. The present disclosure features methods of identifying nitration enzymes, including methods of purification and characterization. Additionally, the present disclosure includes the use of nitration enzymes in screening for inhibitors, e.g., biologics or compounds, e.g., small molecules, that modulate the nitration enzymes.

In an aspect, the disclosure features a method of purifying α-synuclein nitration enzyme, the method including: (a) providing a first composition including α-synuclein nitration enzyme; (b) providing a second composition by contacting a buffer adjusted to a pH of from 7.0 to 8.0 with the first composition; (c) eluting the second composition through a Q SEPHAROSE® column; and (d) washing the Q SEPHAROSE® column with an inorganic salt solution.

In some embodiments, the buffer has a pH of 7.5. In some embodiments, the buffer is a lysis buffer.

In another aspect, the disclosure features a method of purifying α-synuclein nitration enzyme, the method including: (a) providing a first composition including α-synuclein nitration enzyme; (b) providing a second composition by contacting a buffer adjusted to a pH of from 5.5 to 6.5 with the first composition; (c) eluting the second composition through a SP SEPHAROSE® column; and (d) washing the SP SEPHAROSE® column with an inorganic salt solution.

In some embodiments, the buffer has a pH of 6.0. In some embodiments, the buffer is a sodium acetate buffer.

In some embodiments, the inorganic salt solution is a NaCl solution.

In another aspect, the disclosure features a method of purifying α-synuclein nitration enzyme, the method including: (a) providing a first composition including α-synuclein nitration enzyme; (b) providing a second composition by heating the first composition to a temperature between 65° C. and 75° C.; (c) centrifuging the second composition; and (d) isolating the supernatant of the second composition, where the supernatant includes partially purified α-synuclein nitration enzyme.

In some embodiments, the temperature is 70±2° C.

In yet another aspect, the disclosure features a method of purifying α-synuclein nitration enzyme, the method including: (a) providing a first composition including α-synuclein nitration enzyme; (b) providing a second composition by contacting a buffer with the first composition; (c) providing a third composition by eluting the second composition through a Q SEPHAROSE® column; (d) providing a fourth composition by eluting the third composition through a SP SEPHAROSE® column and/or a SUPERDEX® 75 10/300 GL column; and (f) washing the SP SEPHAROSE® column and/or a SUPERDEX® 75 10/300 GL column with a buffer, where the third composition is optionally heated to a temperature between 65° C. and 75° C.

In some embodiments, the buffer includes tris(hydroxymethyl)aminomethane (Tris). In some embodiments, the buffer includes 100 mM of Tris. In some embodiments, the buffer has a pH from 7.0 to 8.0. In some embodiments, the buffer has a pH of 7.5.

The nitration enzyme provides specific enzyme targets and active sites against which high-affinity compounds or biologics can be developed to inhibit down-stream deleterious events. This allows for treatment or prevention of age-dependent diseases that do not broadly inhibit free radical damage. Compounds that inhibit free radical damage, such as spin traps, can be overwhelmed by the high abundance and concentration of radicals generated during aging or in pathological disease states. Targeting the inhibition of the α-synuclein nitration enzyme through selective, high affinity compounds, e.g., small molecules would lead to more potent therapeutics without the issues which have limited the utility of non-specific inhibitors of free radicals.

An additional implication beyond the development of therapeutics is the identification of a new enzyme and/or class of enzymes that nitrate their substrates and mediate posttranslational changes in their structure and/or function in a manner that is similar to protein kinases phosphorylating their substrates. The relevance of these modifications has been demonstrated for α-synuclein structure and tyrosine hydroxylase activity in PD but nitration is also prevalent in AD, cancer, stroke, heart attack, and aging. By identifying this new class of enzymes, a new field to determine their relevance in normal and disease states is opened and novel opportunities for drug discovery efforts to treat them are created.

In an aspect, the disclosure features a method of identifying a compound that inhibits nitration enzyme, the method including: (a) providing a first composition including a peptide, peroxynitrite, and nitration enzyme; (b) providing a second composition by contacting a compound with the first composition; and (c) identifying the level of nitrated synuclein in the second composition, where a reduction in the level of nitrated synuclein indicates a compound that inhibits the nitration enzyme.

In some embodiments, the peptide is α-synuclein. In some embodiments, the peptide is a synuclein peptide containing tyrosine nitrated by synuclein nitrase or any one of SEQ ID NOS: 1-4. In some embodiments, the nitration enzyme is α-synuclein nitration enzyme. In some embodiments, identifying the level of nitrated synuclein includes: (i) contacting the second composition with a nitrated synuclein antibody; and (ii) measuring the optical density of the level of nitrated synuclein. In some embodiments, the compound includes a nitromethane moiety. In some embodiments, the compound includes a peroxynitrite moiety.

Definitions

As used herein, the term "nitromethane moiety" refers to a moiety including the following structure:

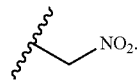

As used herein, the term "peroxynitrite moiety" refers to a moiety including the following structure:

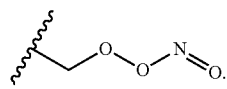 [SMILES: *COON=O]

As used herein, the term "nitration enzyme" refers to an enzyme that modulates (e.g., increases) the level of nitration of a protein. In some embodiments, the nitration enzyme is a tyrosine nitration enzyme that can selectively nitrate one or more (two or more, three or more, four or more, or five or more) tyrosine residues of a protein. The level of nitration can be determined by assessing changes in (i) the level of proteins that are at least partially nitrated, or (ii) the number of tyrosine nitrations in a mixture containing at least partially nitrated proteins. In particular embodiments, the protein is α-synuclein, or any other protein or peptide described herein.

As used herein, the term "therapeutically effective amount" refers to an amount sufficient to produce a desired result, for example, the inhibition of synuclein nitration enzyme or treatment of a disease related to synuclein nitration, e.g., neurodegenerative diseases, e.g., Parkinson's disease.

DETAILED DESCRIPTION

Figure 1:
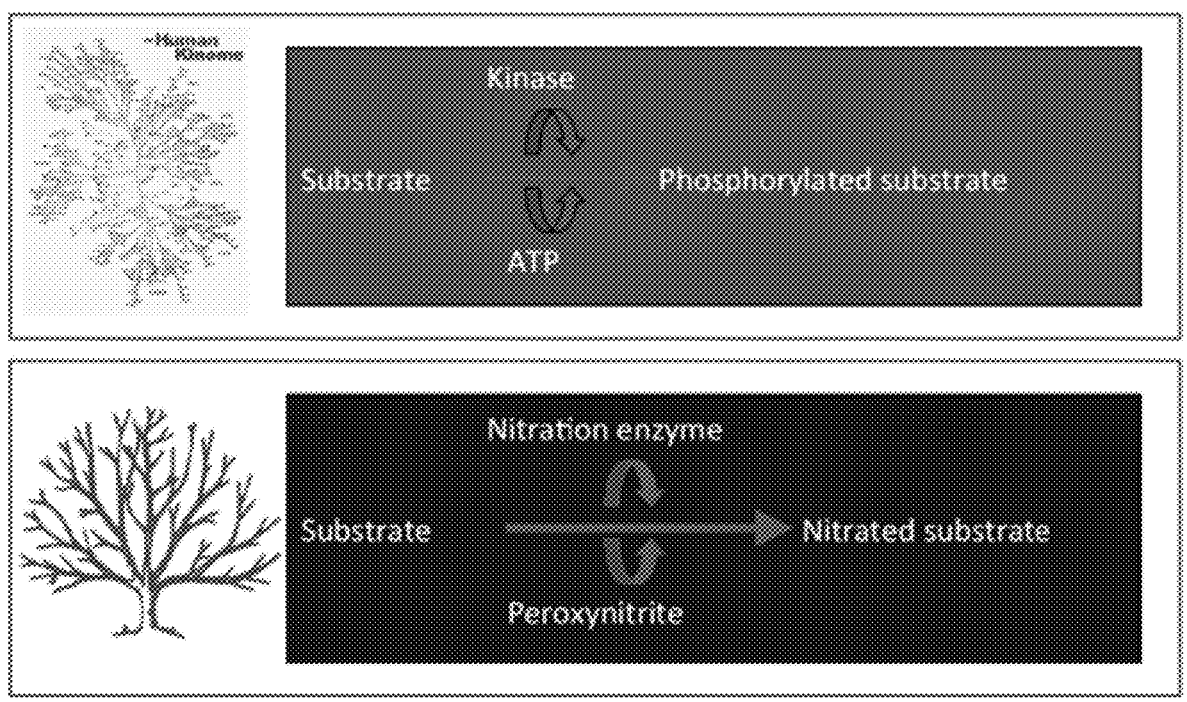
FIG. 1 is a diagram comparing the activity of kinases (top) to a nitration enzyme (bottom).

The present disclosure features nitration of α-synuclein is enzyme-dependent and can be inhibited by a compound, e.g., a small molecule which would slow or block α-synuclein-dependent neurodegeneration. The present invention features methods of identifying nitration enzymes including purification and characterization. It also includes the use of nitration enzymes in screening for compounds that modulate the nitration enzymes including compounds, e.g., small molecules and biologics.

Enzymes have historically been very druggable targets. The nitration enzyme provides a specific enzyme target and active site against which high-affinity small molecules can be developed to inhibit down-stream deleterious events. This allows for treatment or prevention of age-dependent neurodegenerative diseases that do not broadly inhibit free radical damage. Compounds that inhibit free radical damage, such as spin traps can be overwhelmed by the high abundance and concentration of radicals generated during aging or in pathological disease states. Targeting the inhibition of the synuclein nitration enzyme through selective, high affinity small molecules would lead to more potent therapeutics without the issues which have limited the utility of non-specific free radical inhibitors.

An additional implication beyond the development of therapeutics is the identification of a new enzyme and/or class of enzymes that nitrate their substrates and mediate posttranslational changes in their structure and/or function in a manner that is similar to protein kinases phosphorylating their substrates. The relevance of these modifications has been demonstrated for α-synuclein structure and tyrosine hydroxylase activity in PD but additionally nitration is also prevalent in AD, cancer, stroke, heart attack, and aging. By identifying this new class of enzymes, we open up a new field to determine their relevance in normal and disease states and create novel opportunities for drug discovery efforts to treat them.

The present disclosure preliminarily demonstrates the existence of substoichiometric protein-dependent nitration and dityrosine crosslinking of α-synuclein and features a robust α-synuclein nitration assay that will be used to identify the enzyme. This nitration assay will allow for screening for inhibitors (e.g., compounds (e.g., small molecules) or biologics) of the α-synuclein nitration enzyme to identify potential therapeutic candidates. The nitration assay also allows for identifying the sequence of the purified α-synuclein nitration enzyme using conventional protein sequencing techniques and measuring α-synuclein nitration activity. The protein or proteins responsible for α-synuclein nitration activity could represent a new class of drug targets.

Furthermore, the present disclosure demonstrates that the α-synuclein nitration enzyme can be inhibited using a compound, e.g., a tool compound.

The α-synuclein nitration assay described herein can be used with active fractions from the purification scheme shown in Example 7 to screen an HTS library to identify additional hits.

Once identified the α-synuclein nitration enzyme-modulating biologics or compounds, e.g., small molecules would be tested using routine preclinical and clinical methods to determine efficacy and safety in treating disease, e.g. neurodegenerative disease, e.g., Parkinson's disease. Preferred synuclein nitrating enzyme modulating molecules will have a high affinity for the binding site on the synuclein nitrating enzyme, a high level of inactivation of the synuclein nitrating enzyme, will remain bound under normal physiological conditions. Additionally, the preferred synuclein nitrating enzyme modulating molecules will have an acceptable toxicity for the disease being treated.

In addition to a classical small molecule approach, biologics can be created which are synuclein nitrating enzyme modulating molecules. Such biologics can be RNA, DNA, or protein based. A preferred approach will be to develop antibodies to the synuclein nitrating enzyme using conventional techniques and screening the antibodies for preferred activity and low toxicities. Such antibodies can be characterized by protein sequence, binding affinity and structure of the binding domain.

Synuclein nitrating enzyme modulating compounds can be administered via routes known in the art. Common routes of administration include oral, buccal, injection, intraperitoneal, and rectal. Dosage forms can be immediate or controlled release formulations. The dosing schedule can be determined through routine clinical testing. Dosage amounts will be determined prior to human clinical testing through animal testing to determine levels at which the synuclein-nitrating enzyme modulating molecules are safe and/or effective.

Suitable animal models include rodent, canine and primates. Suitable disease indications include neurological disorders such as Parkinson's, amyotrophic lateral sclerosis, Alzheimer's and Huntington's. The use of synuclein-nitrating enzyme modulating molecules early in the treatment of these disorders will likely prevent, slow progression, or reverse the disease. Additional disease indications include cancer, cardiovascular and stroke. The use of nitration enzyme modulating molecules early in the treatment of these disorders will likely prevent, slow progression, or reverse the disease.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

EXAMPLES

The following examples are illustrative of aspects and embodiments of the present invention. These examples put forth to provide those of ordinary skill in the art with a description of how the methods described herein may be used, made, and evaluated, and are intended to be purely exemplary of the invention and are not intended to limit the scope of what the inventors regard as their invention.

Example 1—Temperature Dependency of Nitration in Cells

This example demonstrates the temperature-dependence of the nitration of proteins in an intact cell and supports a protein-dependent and/or energy-dependent nitration reaction.

Background: Although oxidative and/or nitrative stress-induced modification of proteins is robustly observed in neurodegenerative diseases, e.g., Parkinson's disease, only a few specific proteins are nitrated. This small subset of proteins is consistently nitrated in various models of PD and in neuronal tissue from PD and other synucleinopathies. These proteins include α-synuclein and tyrosine hydroxylase, two critical proteins involved in PD. At least one specific entity (e.g., one entity, two entities, three entities, four entities, five entities, or more) could help guide and direct the nitration of these particular proteins.

While the current dogma suggests that chemical reactivity alone is responsible for protein nitration, this example suggests that a nitration enzyme can catalyze nitration and/or amplify chemical nitration. This concept is demonstrated in FIG. 1. Similar to how kinases transfer a phosphate group from ATP to their substrates (FIG. 1, top), nitration enzymes could transfer a nitrate group and/or facilitate tyrosine free radical formation to induce dityrosine crosslinking (FIG. 1, bottom). The data in this example supports this hypothesis.

Figure 2:
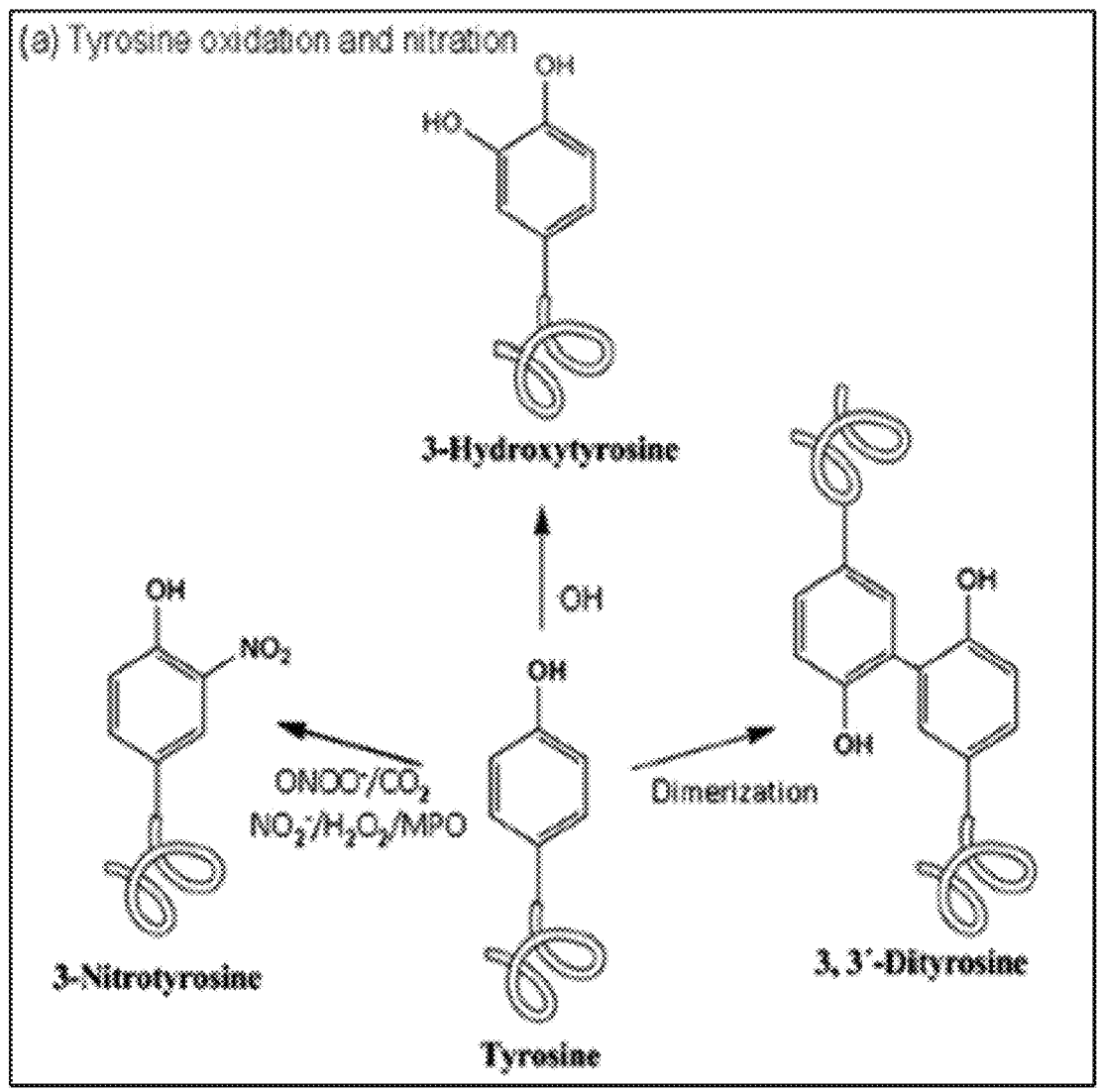
FIG. 2 is a reaction scheme from the prior art showing that peroxynitrite interacts with a tyrosine residue to generate a free radical.

FIG. 2 illustrates how peroxynitrite-dependent protein nitration reactions occur (adapted from Chavarria et al., Arch. Biochem. Biophys. 533(1-2):25-32 (2013)). Peroxynitrite interacts with a tyrosine residue to generate a free radical that is reactive and can facilitate either protein 3-nitrotyrosine or dityrosine crosslinking with a second nearby tyrosine residue. Since peroxynitrite can generate either of these tyrosine end products, both of these endpoints were analyzed in this example.

Methods: SH-SY5Y neuroblastoma cells were pre-incubated either at 0° C. or 37° C. to bring the cells to the corresponding temperatures. The SH-SY5Y cells were then incubated without peroxynitrite or with either a 111 μM, 333 μM, or 1000 μM peroxynitrite solution. The peroxynitrite was added to the media for 10 minutes. A cell lysate was generated by lysing the treated cells with 1 mL/10 cm plate of 50 mM Tris (pH 7.5), 20 mM NaCl, 0.1% TRITON® X-100, and Cell-Signaling Technology protease inhibitor cocktail (#5872). Particulates were spun down at 15,000 rpm for 15 minutes at 4° C. and cleared supernatants collected (lysate). SDS-PAGE sample buffer was added to the lysates, and the protein was separated on 10-20% Tricine SDS-PAGE gel electrophoresis. The proteins in gels were then transferred to Immobilon. Immobilon membranes were incubated in 4% BSA/0.2% TWEEN®-20/TBS for 2 hours at room temperature. The membranes were then incubated with 1 μg/mL anti-nitrosynuclein antibody 10G5 (Elan Pharmaceuticals) in TBS buffer with 0.2% TWEEN®-20 for 1 hour, followed by 5000×HRP-anti-mouse secondary antibody (Amersham #GENXA931). Subsequently, the membranes were treated for ECL (enhanced chemiluminescence) and exposed to film.

Figure 3:
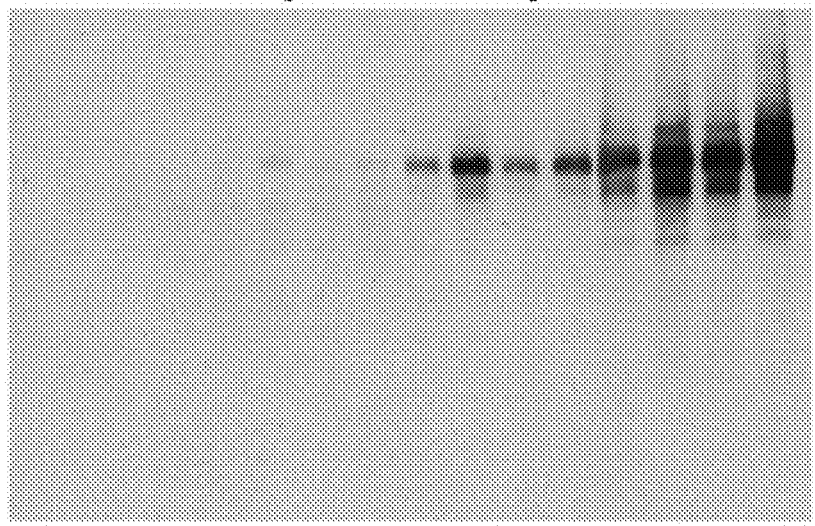
FIG. 3 illustrates Western blots showing temperature dependency of nitration in cells.

Results: As shown in FIG. 3, the cellular lysates show a strong peroxynitrite-dependent and temperature-dependent protein nitration. The inset below the Western blot shows a 14 kd protein, whose molecular weight is consistent with α-synuclein, which is strongly nitrated in a temperature-dependent manner. This suggests a protein-dependent and/or energy-dependent protein nitration in intact cells.

Example 2—Addition of Protein Preparations Containing the α-Synuclein Nitration Enzyme This example demonstrates that addition of protein preparations containing the α-synuclein nitration enzyme induce α-synuclein nitration and the formation of α-synuclein aggregates and/or dityrosine crosslinks.

Methods: SH-SY5Y neuroblastoma cell cytosolic fractions were obtained by lysing SH-SY5Y cells with 1 mL/10 cm plate of 50 mM Tris (pH 7.5), 20 mM NaCl, and Cell Signaling Technology protease inhibitor cocktail (#5872). Particulates were spun down at 15,000 rpm for 15 minutes at 4° C. and supernatants containing the cytosolic fraction (Protein Prep #1) were collected. To obtain the Q SEPHAROSE® flow through fraction, the SH-SY5Y cytosol was applied onto a Q SEPHAROSE® column and flow through fraction (Protein Prep #2) was collected.

The α-synuclein nitration assay was run in a round bottom plate (ThermoFisher #2205) with final concentrations of 3.6 μM α-synuclein (rPeptide #5-1001), 50 mM Tris (pH 7.5), and 20 mM NaCl or 12 μg SH-SY5Y cytosol or 12 μg Q SEPHAROSE® flow through fraction. The reactions were started by addition of 100 μM peroxynitrite. These reactions were run at 37° C. for 10 minutes. The reactions were stopped by adding SDS-PAGE sample buffer, and the proteins were separated by 10-20% Tricine SDS-PAGE gel electrophoresis. The proteins in gels were transferred to Immobilon membranes. Immobilon membranes were incubated in 4% BSA/0.2% TWEEN®-20/TBS for 2 hours at room temperature, followed by incubation in either 1 µg/mL anti-synuclein antibody Syn-1 (BD Transduction Labs) (left) or 1 µg/mL anti-nitrosynuclein antibody 10G5 (Elan Pharmaceuticals) in TBS buffer with 0.2% TWEEN®-20 for 1 hour followed by 5000×HRP-anti-mouse secondary antibody (Amersham #GENXA931). Subsequently, the membranes were treated for ECL (enhanced chemiluminescence) and exposed to film.

Figure 4:
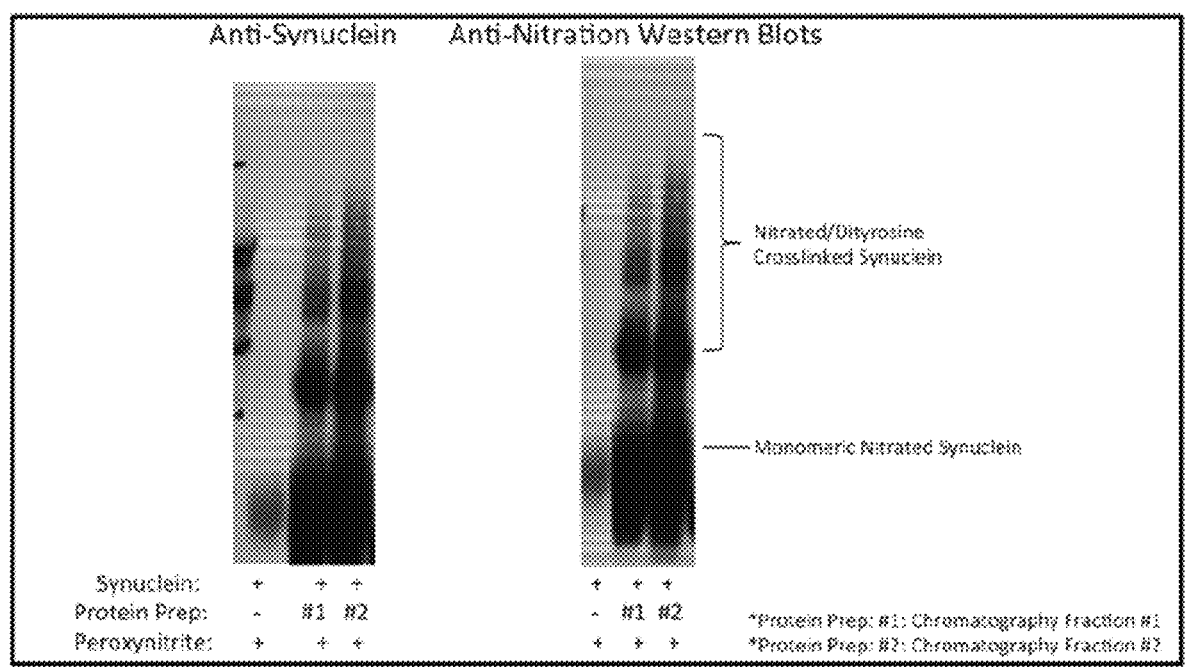
FIG. 4 is a Western blot showing α-synuclein aggregates/dityrosine crosslinks (left) and α-synuclein nitration (right) are induced substantially with the addition of protein preparations containing the α-synuclein nitration enzyme.

Results: FIG. 4 shows that α-synuclein nitration (left) and a synuclein aggregates/dityrosine crosslinks (right) are induced substantially with the addition of protein preparations containing the α-synuclein nitration enzyme.

Example 3—Intact, Boiled Lysates and Peroxynitrite-Dependent α-Synuclein and Dityrosine Crosslinking This example demonstrates experiments conducted to determine if intact versus boiled lysates cause peroxynitrite-dependent α-synuclein and dityrosine crosslinking.

Methods: Additional experiments were conducted to determine if proteins are required for the lysate-dependent reaction. First, the SH-SY5Y lysate (prepared as described in Example 1, FIG. 3) was boiled for 5 minutes, and the precipitated constituents were removed by centrifugation at 14,000 rpm for 15 minutes. The boiled lysate supernatant was compared to intact lysate in the nitration reaction assay conducted as described in Example 2, FIG. 4 with the exception that 0 µM, 10 µM, or 100 µM peroxynitrite was used in the reaction. This was followed by anti-α-synuclein Western blot (run as described in Example 2, FIG. 4).

Figure 5:
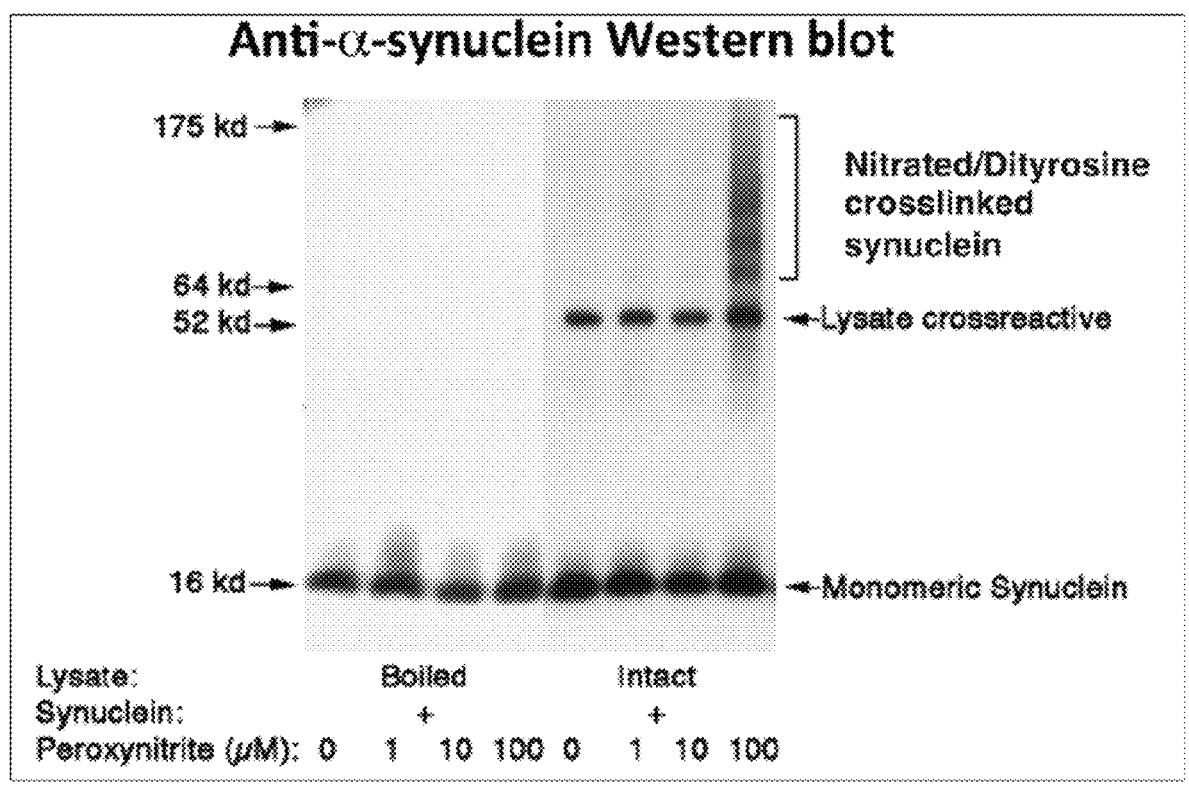
FIG. 5 is a Western blot showing intact, not boiled, lysate causes peroxynitrite-dependent α-synuclein dityrosine crosslinking.

Results: As shown in FIG. 5, intact lysate causes peroxynitrite-dependent α-synuclein dityrosine crosslinking, while boiled lysate does not.

Example 4—Intact, Trypsinized Lysates and Peroxynitrite-Dependent α-Synuclein and Dityrosine Crosslinking This example demonstrates experiments conducted to determine if intact versus trypsinized lysates cause peroxynitrite-dependent α-synuclein and dityrosine crosslinking.

Methods: The lysate was incubated with or without 1:50 (wt/wt, trypsin:protein) trypsin for 1 hour at room temperature, trypsin was inactivated by addition of 1 mM PMSF to lysates, and lysates added to the nitration reaction assay (run as described in Example 2, FIG. 4, with the exception that 0 µM, 10 µM, or 100 µM peroxynitrite was used) and processed by anti-α-synuclein Western blot (described in Example 2, FIG. 4).

Figure 6:
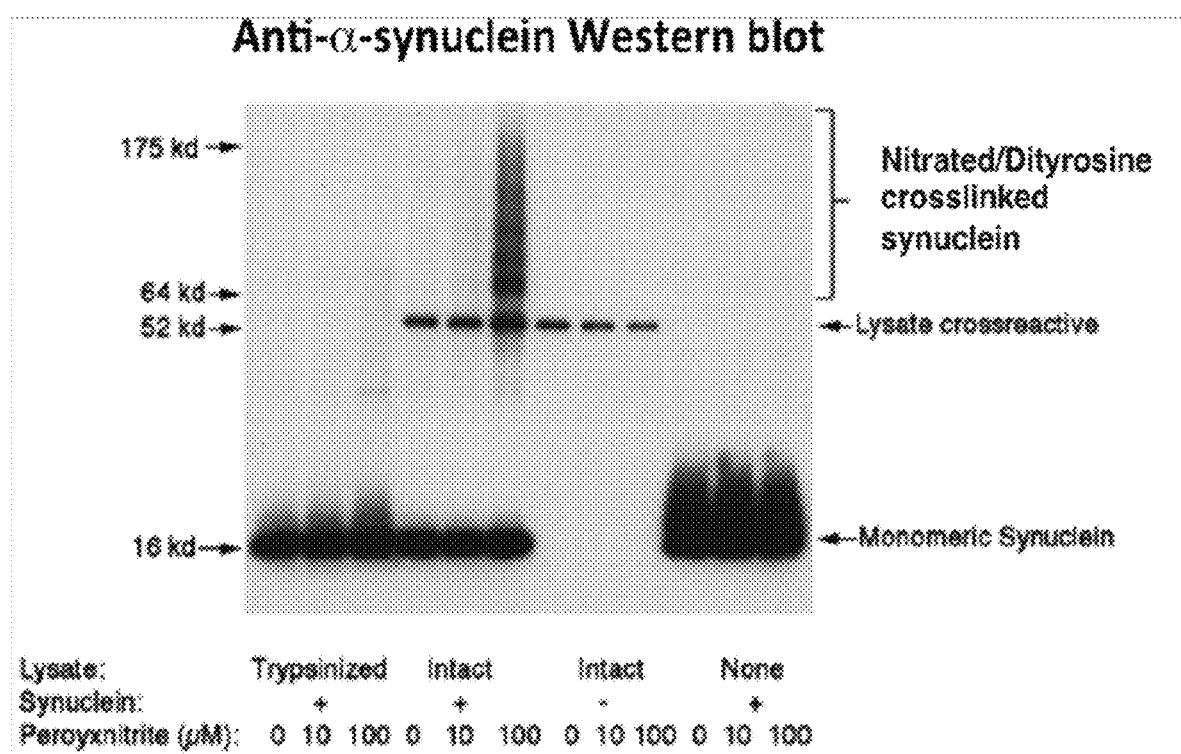
FIG. 6 is a Western blot showing intact lysate causes peroxynitrite-dependent α-synuclein dityrosine crosslinking.

Results: As shown in FIG. 6, intact, not trypsinized, lysate causes peroxynitrite-dependent dityrosine crosslinking of α-synuclein.

Examples 3 and 4 demonstrate that both boiling and trypsinization inhibited α-synuclein nitration and dityrosine crosslinking, which supports that α-synuclein nitration is a protein-dependent reaction.

Example 5—Intact, not Boiled Lysate and Peroxynitrite-Dependent α-Synuclein and Dityrosine Crosslinking This example demonstrates experiments conducted to determine if a specific, not a random protein is required to cause peroxynitrite-dependent dityrosine α-synuclein crosslinking.

Methods: The methods were similar to Example 2, except 12 µg BSA or 12 µg lysate was incubated in the reactions. This was processed by anti-α-synuclein Western blot (as described in Example 2, FIG. 4). Proteins that have previously been reported to nitrate substrates such as fALS mutant SOD1 or proteins that might nitrate substrates, such as MPO, were also tested: 12 µg SOD1 or MPO compared to 12 µg lysate with 0 µM, 25 µM, 50 µM, or 100 µM peroxynitrite but were not capable of nitrating α-synuclein in this assay.

Figure 7:
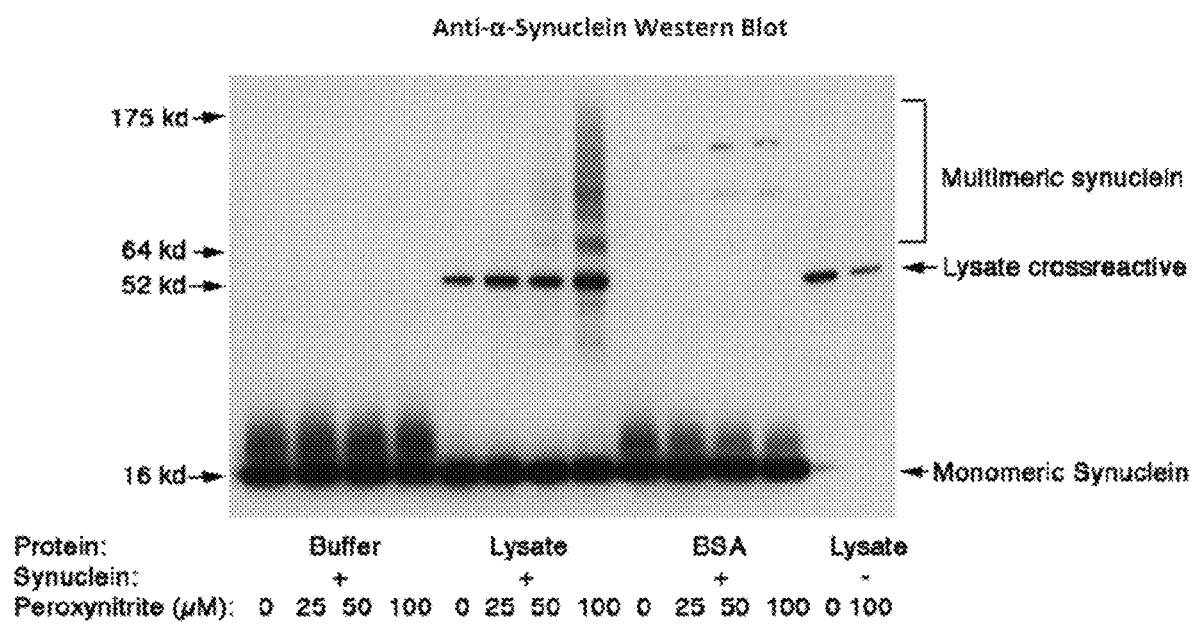
FIG. 7 is a Western blot showing that a protein, such as bovine serum albumin (BSA), does not induce peroxynitrite-dependent dityrosine α-synuclein crosslinking.

Results: As shown in FIG. 7, a specific, and not a random protein, such as BSA, SOD, or MPO, is required to cause peroxynitrite-dependent dityrosine crosslinking of α-synuclein.

Example 6—Elution Profile of α-Synuclein from a Monomeric Elution Profile in the Absence of Added Lysate This example demonstrates experiments conducted to determine if the protein-dependent α-synuclein nitration is enzyme-mediated.

Methods: A nitration reaction assay using a 4:1 ratio of lysate was conducted with α-synuclein, as described in Example 2, FIG. 4, in order to determine whether the lysate altered the mobility of a majority of α-synuclein, which is consistent with dityrosine crosslinking of α-synuclein.

The nitration reactions were separated with gel filtration chromatography to determine if the lysate shifted the mobility of α-synuclein versus no lysate reactions.

Figure 8:
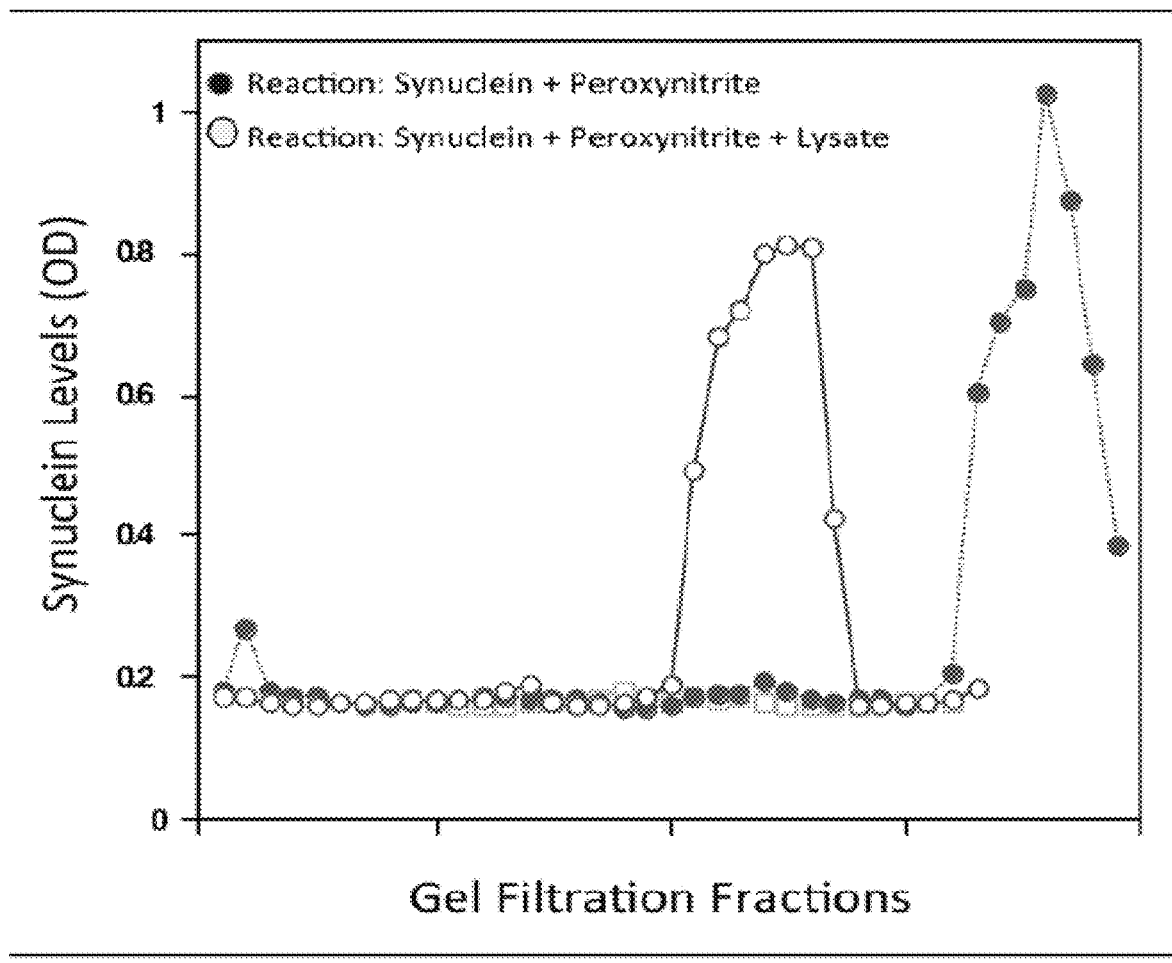
FIG. 8 is a graph showing a complete shift in the elution profile of α-synuclein from a monomeric elution profile in the absence of added lysate to larger molecular weight species (including retention on the column) with added lysate when eluted from gel filtration.

Results: As shown in FIG. 8, there was a complete shift in the elution profile of α-synuclein from a monomeric elution profile in the absence of added lysate to larger molecular weight species (including retention on the column) with added lysate when eluted from gel filtration. This occurs at levels as low as four times the ratio of lysate protein to α-synuclein. If there is a specific protein responsible for this reaction, as suggested by lack of effect by various proteins that were tested, then only a small percentage of the protein in this lysate would contribute to this α-synuclein dityrosine crosslinking and aggregation and would be suggestive of a substoichiometric or catalytic reaction. This was consistent with and helped provide evidence that an enzyme mediates α-synuclein nitration.

Example 7—Purification: Anion Exchange, Cation Exchange, and Hydrophobic Exchange This example demonstrated the development of a reproducible purification protocol to isolate the protein responsible for enhancing α-synuclein nitration.

Methods: The purification process consists of anion exchange followed by cation exchange and then hydrophobic exchange chromatography. These conditions have been optimized and elution properties identified through multiple isolations to show that the procedure is highly reproducible. The cytosolic fraction from SH-SY5Y cell (described in Example 2, FIG. 4) was applied to Q SEPHAROSE® column and fractions run in the nitration assay (described in Example 2, FIG. 4) that showed that the α-synuclein nitrating activity was in the Q SEPHAROSE® flow through fraction. The Q SEPHAROSE® flow through was then applied to a Mono S cationic exchange column using FPLC to generate reproducible elution profiles and α-synuclein nitration activity was measured in each fraction (same reaction conditions as described in Example 2, FIG. 4).

α-Synuclein nitration was measured in this example using a nitrosynuclein ELISA (instead of Western blots). First, ELISA plates (ThermoFisher #439454) was coated with 1 µg/mL nitrosynuclein antibody 10G5 (Elan Pharmaceuticals) in TBS, incubated 1 hour at room temperature, blocked with casein for 1 hour room temperature, and washed with 4×200 µL TBS/0.2% TWEEN®-20 (TBST). Then α-synuclein nitration assay samples were added to the coated plates and incubated overnight at 4° C. The plates were washed 4× with 200 µL TBST, followed by incubation with 1 µg/mL biotinylated Syn-1 (BD Transduction) in casein for 60 minutes at room temperature. The plates were then washed 4× with TBST and incubated with 2500× dilute Vector #A-2004 HRP-streptavidin/casein for 30 minutes at room temperature. Next, the plates were washed 4× with TBST. Subsequently, 50 µL of TMB (ThermoFisher #34024) was added, and the plates were incubated for 15 minutes at room temperature. Finally, 50 µL/well of 2N sulfuric acid was added to the plates. The optical density (OD) was measured at 450 nm.

Figure 9:
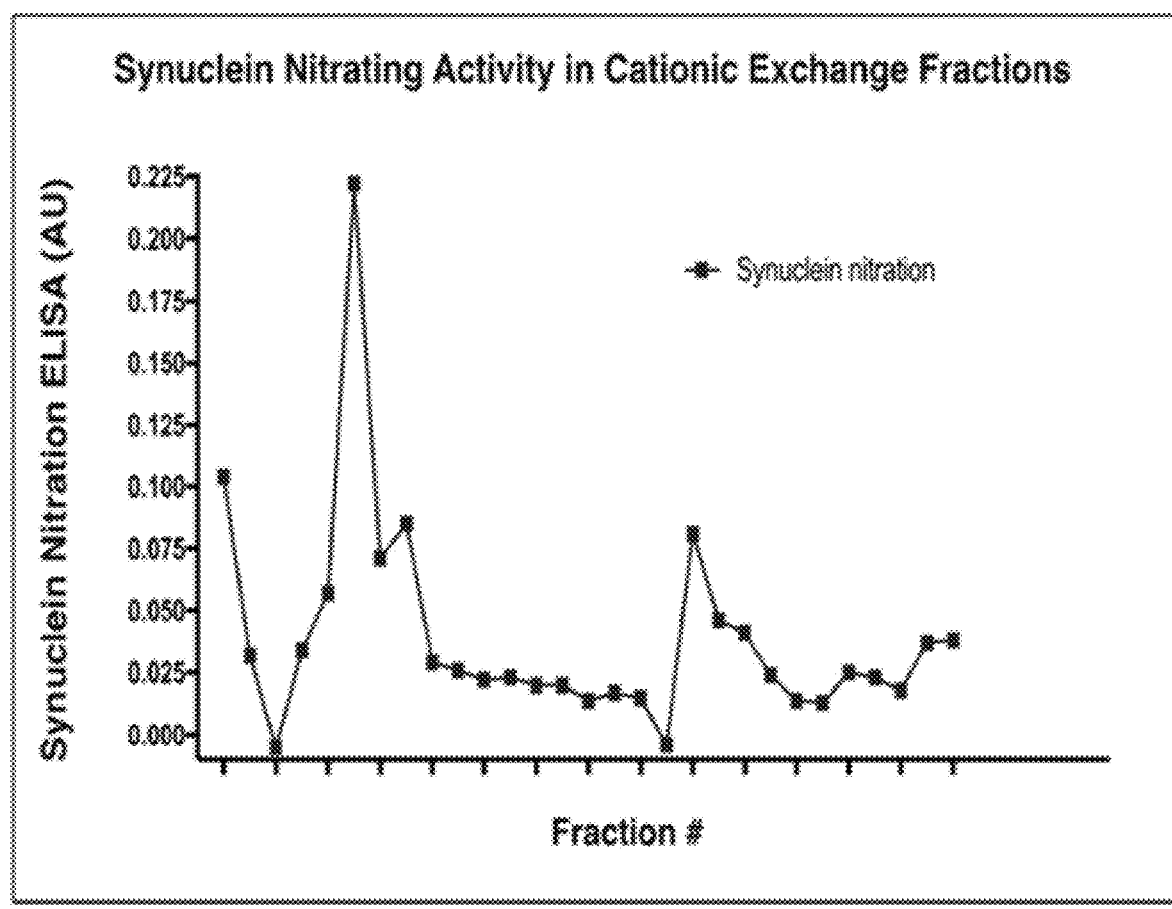
FIG. 9 is a graph showing that a dramatic increase in α-synuclein nitration occurs in one major and one minor peak eluted off the cationic exchange column.

The α-synuclein nitration levels were measured by ELISA as shown in FIG. 9. A dramatic increase in α-synuclein nitration occurs in one major and one minor peak eluted off this column. The proteins in these fractions surrounding the major peak were trypsinized and then incubated in the α-synuclein nitration assay (same trypsinization process as described in Example 4, FIG. 6 and nitration reaction assay conditions as described in Example 2, FIG. 4).

Figure 10:
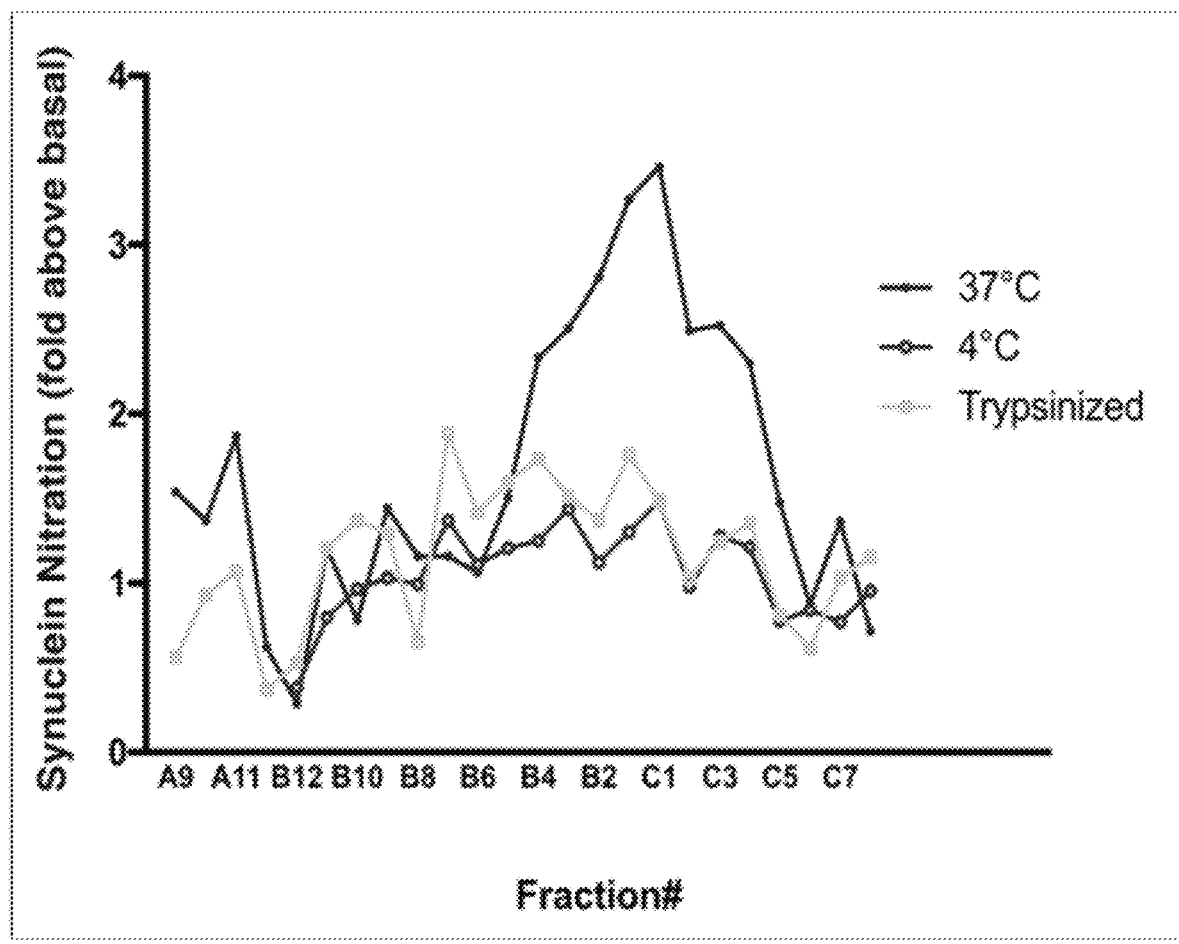
FIG. 10 is a graph showing inhibition of enzyme activity when protein fractions are trypsinized or when the enzyme reactions are conducted at 4° C.

Results: As shown in FIG. 10, trypsinization eliminated α-synuclein nitration activity. Activity was also inhibited when the nitration assays were conducted at 4° C. (same assay as in Example 2, FIG. 4 except the assay was run at 0° C. instead of 37° C. and α-synuclein nitration levels were measured by ELISA as described above).

These data confirm that a protein (or proteins) that mediates a protein-dependent peroxynitrite-dependent nitration of α-synuclein can be purified through several chromatography steps. Protein fractions from the cationic exchange column from pooled active versus inactive fractions were separated by SDS-PAGE gel electrophoresis, and the gel was silver stained (ThermoFisher #24612) to determine how many protein remained in the active α-synuclein nitration fractions at this step in its isolation.

Figure 11:
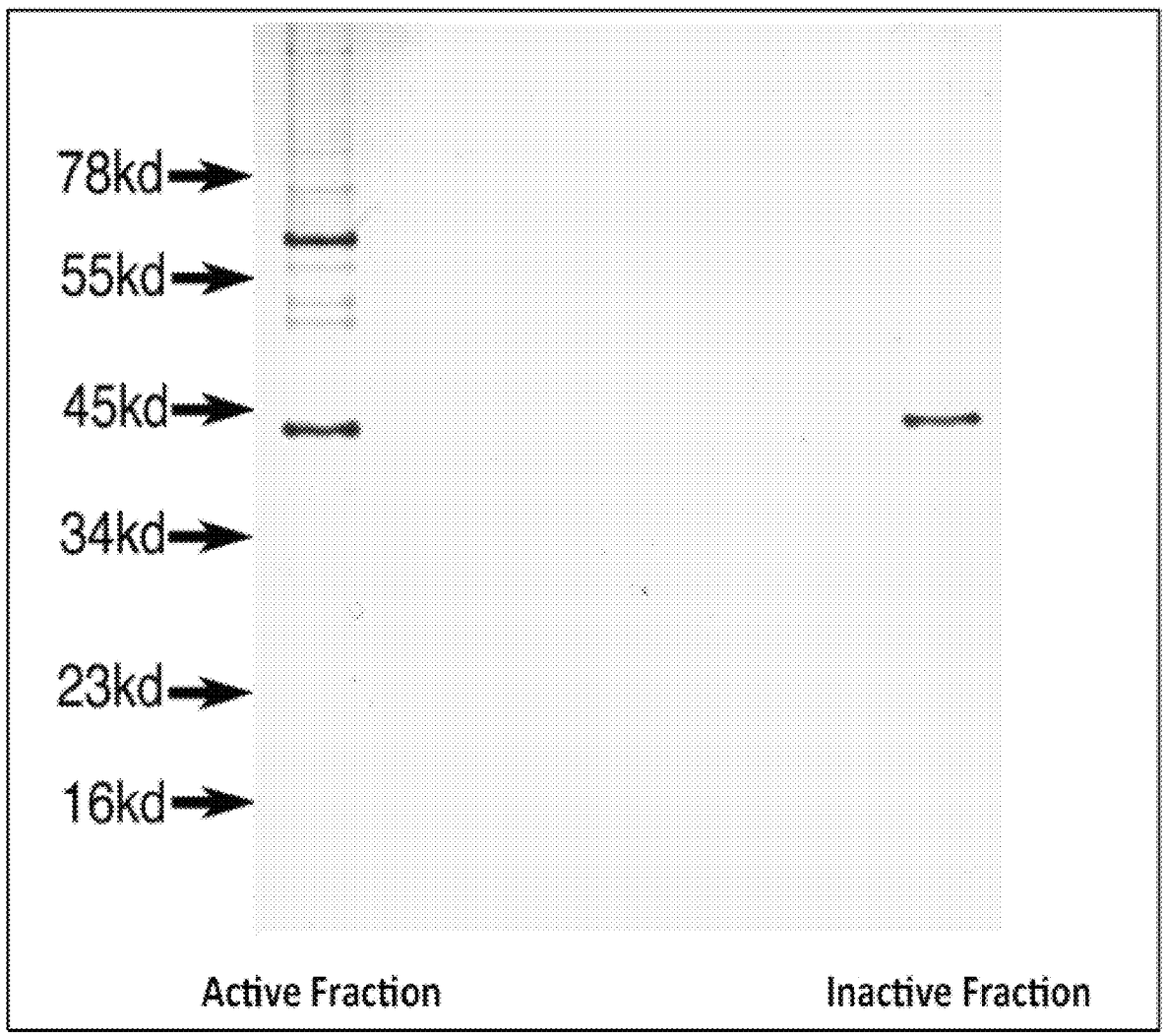
FIG. 11 is a photo of an electrophoresis gel showing the active fraction contains a small number of proteins visible by silver staining.

As shown in FIG. 11, the active fraction contains a small number of proteins visible by silver staining. This suggested that one or two additional chromatography steps are necessary to purify this enzyme to homogeneity.

The major peak of α-synuclein nitrating activity from the cationic exchange column, therefore, was pooled and applied to a hydrophobic exchange column and a major α-synuclein nitration activity identified in fractions eluted from this column. These three chromatography steps have been repeated multiple times to ensure reproducibility of the isolation process for the α-synuclein nitration enzyme. The yield is low at the hydrophobic exchange and thus, the isolation is being conducted from brains from rats and bovine to ensure sufficient yield at the end of the purification steps.

Example 8—Nitration of α-Synuclein Biotinylated Peptide: One-Pot ELISA

The following example demonstrates the nitration of α-synuclein peptide with and without the Q FT fractions. A one-pot ELISA (enzyme-linked immunosorbent assay) was used to detect the levels of nitrated α-synuclein peptide.

Materials: The materials and reagents used in this example are as follows:

| Reagent | Vendor | Catalog No. |
|---|---|---|
| α-synuclein Biotinylated Peptide 7, 1.0 mg/mL aa 130-139, Biotin-EEGYQDYEPE (SEQ ID NO: 1) Biotin-SEEGYQDYEPEA (SEQ ID NO: 2) | AbClonal | P180625-CJ663064 |
| Peroxynitrite | EMD Millipore | 20-107 |
| NaOH,10.0N | Spectrum | S-395 |
| Tris, pH 8.0, 1.0M | Biovision | 2107-100 |
| Q Flow through of rat brain | Rockland | RT-T077 |
| Streptavidin-coated ELISA plate | ThermoFisher | 15120 |
| Anti-nitro-α/β-Synuclein Antibody, clone nSyn12 | EMD Millipore | 36-011 |
| Anti-mouse IgG HRP | Novus Biological | NBP2-30347H |
| 10X TBS | BioBasic | A0027 |
| TMB substrate | EMD Millipore | CL07-100ML |
| 10.0N sulfuric acid | Millipore | 1.60315.1000 |

Methods:

Preparation of Reagents: A 110 mM stock solution of peroxynitrite (ONOO⁻) was diluted so that a final concentration in reactions of 100 µM was generated by adding 1.5 µL to 80 µL of 0.3 M NaOH; 500 µM by adding 2.47 µL to 24.70 µL of 0.3 M NaOH; and 1000 µM by adding 4.94 µL to 22.23 µL of 0.3 M NaOH.

A solution of nSyn12 nitrated α-synuclein antibody (1.0 µg/mL) (nSyn12 mAb solution) was prepared by adding 2.0 µL of 1.0 mg/mL stock solution to 1998 µL of Assay Buffer (0.1% casein/TBS).

ELISA Plate: A Streptavidin-coated ELISA plate was treated with 100 µL/well of 2.5 µg/mL of SEQ ID NO:1 or SEQ ID NO: 2. The plate was sealed and incubated on a plate shaker at 400 rpm for 1 hour at room temperature. Then the ELISA plate was washed 2× with 300 µL/well of 1×TBS buffer.

Nitration Reaction Conditions: The following nitration reactions (40 µL) were set up in the wells of the ELISA plate:

| Condition | Plate Wells | ONOO⁻ or NaOH (µL) | [ONOO⁻] (µM) | 100 mM Tris-HCl, pH 8.8 (µL) | Q FT 4 mg/mL (µL) |
|---|---|---|---|---|---|
| 1 | A1-B1 | 2 | 0 | 38 | 0 |
| 2 | C1-D1 | 2 | 100 | 38 | 0 |
| 3 | E1-F1 | 2 | 500 | 38 | 0 |
| 4 | G1-H1 | 2 | 1000 | 38 | 0 |
| 5 | A2-B2 | 2 | 100 | 37 | 1 |
| 6 | C2-D2 | 2 | 100 | 36.5 | 1.5 |

-continued

| Con-dition | Plate Wells | ONOO⁻ or NaOH (μL) | [ONOO⁻] (μM) | 100 mM Tris-HCl, pH 8.8 (μL) | Q FT 4 mg/mL (μL) |
|---|---|---|---|---|---|
| 7 | E2-F2 | 2 | 100 | 36 | 2 |
| 8 | G2-H2 | 2 | 100 | 35.5 | 2.5 |

First, the Tris buffer and Q FT were added to the wells and mixed. The plate was sealed and placed in a 37° C. water bath for 5 minutes. The plate was then removed from the bath and placed into a Styrofoam box filled with 1 inch of 37° C. water. The seal was removed and the peroxynitrite was quickly added to the corresponding wells. The plate was immediately sealed, lightly tapped to mix the reagents, and placed back in the 37° C. water bath. The plate was lightly tapped every 30 seconds for the first 4 minutes and then every minute until 10 minutes had elapsed. The nitration reaction volume was then removed and the plate was washed 5× with 300 μL/well of 1×TBST (0.05% TWEEN®-20) buffer. The 1× TBS buffer was removed from the ELISA plate by inverting and tapping the plate.

Addition of Antibody: Then 100 μL of the nSyn12 mAb solution was added to each well. The plate was sealed and incubated for 1 hour at room temperature on a plate shaker at 400 rpm. The nSyn12 mAb solution was removed from the ELISA plate by inverting and tapping the plate. The plate was then washed 5× with 300 μL/well of the 1×TBS buffer.

Detection: Then 100 μL of anti-mouse IgG-HRP solution was added to each well. The plate was sealed and incubated for 1 hour at room temperature on a plate shaker at 400 rpm. The anti-mouse IgG-HRP solution was then removed from the ELISA plate by inverting and tapping the plate. The plate was then washed 5× with 300 μL/well of the 1×TBS buffer.

Finally, 50 μL of TMB solution was added to each well. The blue color was developed for 5 to 10 minutes, at which point 50 μL of stop solution (1.0 N sulfuric acid) was added to each well. The absorbance was recorded on a plate reader set at 450 nm with 620 nm subtraction.

Figure 13:
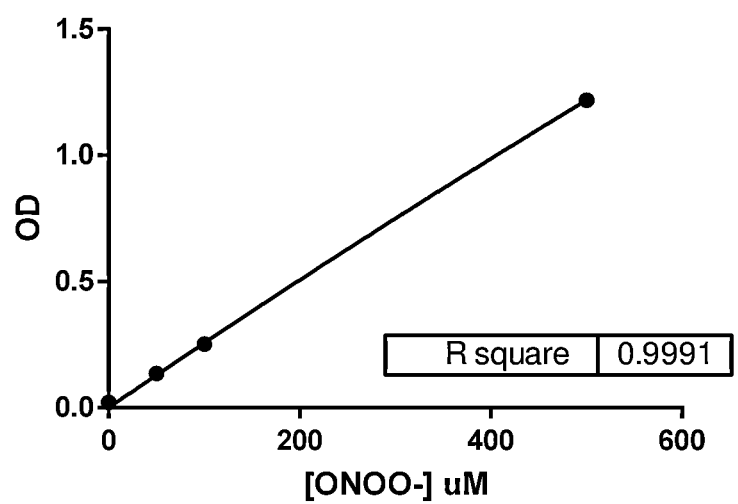
FIG. 13 is a graph showing the chemical nitration of biotinylated α-synuclein in ELISA assay plotted against the concentration of peroxynitrite.

Results: The optical density of nitrated α-synuclein from the chemical nitration conditions with α-synuclein Biotinylated Peptide 7 (SEQ ID NO: 1) were plotted against the concentration of the peroxynitrite (see FIG. 13). The optical density increased linearly as the concentration of peroxynitrite increased.

Figure 14:
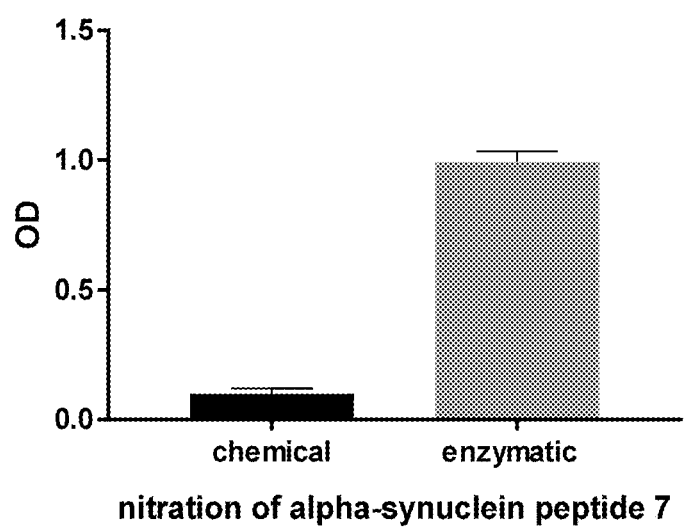
FIG. 14 is a graph showing optical density of nitrated α-synuclein in chemical and enzymatic one-pot nitration conditions of α-synuclein Biotinylated Peptide 7 with 100 µM peroxynitrite in an ELISA assay.

The optical densities of nitrated α-synuclein from the chemical nitration with 100 μM peroxynitrite and the enzymatic (8 mg of Q FT) nitration with 100 μM peroxynitrite are shown in FIG. 14. The optical density of nitrated α-synuclein from the enzymatic nitration was about 10× the optical density of nitrated α-synuclein from the chemical nitration. This data supports that nitration of α-synuclein is enzyme-dependent.

Example 9—Nitration of α-Synuclein Biotinylated Peptide: AlphaLISA

The following example demonstrates the nitration of α-synuclein with and without the Q FT fractions. A PE AlphaLISA (no-wash ELISA assay alternative) protocol was used to detect the levels of nitrated α-synuclein.

Materials: The materials and reagents used in this example are as follows:

| Reagent | Vendor | Catalog# |
|---|---|---|
| Biotin-SEEGYQDYEPEA (SEQ ID NO: 2) | | |
| α-synuclein, 0.2 mg/mL MDVFMKGLSKAKEGVVAAAEKTKQGVAEAAGKTKEGVLYV GSKTKEGVVHGVATVAEKTKEQVTNVGGAVVTGVTAVAQK TVEGAGSIAAATGFVKKDQLGKNEEGAPQEGILEDMPVDP DNEAYEMPSEEGYQDYEPEA (SEQ ID NO: 3) | rPeptides | S-1001-2 |
| Biotin-EEGYQDYEPE (SEQ ID NO: 4) | | |
| Peroxynitrite | EMD Millipore | 20-107 |
| NaOH,10.0N | Spectrum | S-395 |
| Tris, pH 8.0, 1.0M | Biovision | 2107-100 |
| Q column Flow Through (Q FT) of rat brain | Rockland | RT-T077 |
| 384-well Optiplate | Perkin Elmer | 6007290 |
| Anti-nitro-α/β-Synuclein Antibody, clone nSyn12 | EMD Millipore | 36-011 |
| AlphaScreen Streptavidin Coated Donor Beads, 5 mg/mL | Perkin Elmer | 6.8E+07 |
| AlphaScreen Anti-Mouse IgG Acceptor Beads, 5 mg/mL | Perkin Elmer | AL1056 |
| AlphaLISA 10x Immunoassay Buffer | Perkin Elmer | AL000C |

Methods:

Preparation of Reagents: A 110 mM stock solution of peroxynitrite (ONOO⁻) was diluted so that a final concentration in reactions of 100 μM was generated by adding 1.5 μL to 80 μL of 0.3 M NaOH; 500 μM by adding 2.47 μL to 24.70 μL of 0.3 M NaOH; and 1000 μM by adding 4.94 μL to 22.23 μL of 0.3 M NaOH.

The acceptor beads (100 μg/mL; 10×) were prepared in the dark to avoid degradation by adding 2 μL of 5.0 mg/mL of AlphaScreen anti-mouse IgG acceptor beads to 98 μL of 1× AlphaLISA buffer.

The donor beads (400 μg/mL; 10×) were prepared by adding 8 μL of 5.0 mg/mL of AlphaScreen streptavidin coated donor beads to 92 μL of 1× AlphaLISA buffer.

A solution of nSyn12 nitrated α-synuclein antibody (10 nM; 10×) was prepared as follows: 1.5 μL of 1.0 mg/mL stock solution was added to 998.5 μL of 1× AlphaLISA buffer.

Nitration Reaction Conditions: The following nitration reactions (20 μL) were set up in a round bottom plate:

| Con-dition | Plate Wells | α-synuclein 3.6 mM (μL) | ONOO⁻ or NaOH (μL) | [ONOO⁻] (μM) | 100 mM Tris-HCl, pH 8.8 (μL) | Q FT 4 mg/mL (μL) |
|---|---|---|---|---|---|---|
| 1 | A1-B1 | 1 | 1 | 0 | 18 | 0 |
| 2 | C1-D1 | 1 | 1 | 100 | 18 | 0 |

-continued

| Condition | Plate Wells | α-synuclein 3.6 mM (μL) | ONOO⁻ or NaOH (μL) | [ONOO⁻] (μM) | 100 mM Tris-HCl, pH 8.8 (μL) | Q FT 4 mg/mL (μL) |
|---|---|---|---|---|---|---|
| 3 | E1-F1 | 1 | 1 | 500 | 18 | 0 |
| 4 | G1-H1 | 1 | 1 | 1000 | 18 | 0 |
| 5 | A2-B2 | 1 | 1 | 100 | 17 | 1 |
| 6 | C2-D2 | 1 | 1 | 100 | 16.5 | 1.5 |
| 7 | E2-F2 | 1 | 1 | 100 | 16 | 2 |
| 8 | G2-H2 | 1 | 1 | 100 | 15.5 | 2.5 |

First, SEQ ID NO: 2, biotinylated peptide including α-synuclein (SEQ ID NO: 3), or SEQ ID NO: 4 was added to Tris buffer and Q FT in the wells and mixed. The plate was sealed and placed in a 37° C. water bath for 5 minutes. The plate was then removed from the bath and placed into a Styrofoam box filled with 1 inch of 37° C. water. The seal was removed and the peroxynitrite was quickly added to the corresponding wells. The plate was immediately sealed, lightly tapped to mix the reagents, and placed back in the 37° C. water bath. The plate was lightly tapped every 30 seconds for the first 4 minutes and then every minute until 10 minutes had elapsed. The plate was then removed from the water bath.

Acceptor Beads: Then 10 μL of the reaction was added to 70 μL of 1× AlphaLISA buffer (1/8 dilution) in a new round bottom assay plate. The reagents were mixed well.

Then 4 μL of each 10× reagent was added to each well of the 384-well OptiPlate. The plate was tapped gently to allow reagents to settle to the bottom of each well. Subsequently, 4 μL of each nitrated α-synuclein dilution was added to the corresponding wells. Then 24 μL of 1× AlphaLISA buffer was added to each well, and the plate was tapped to mix well. The plate was then sealed and incubated in the dark for 1 hour at room temperature.

Detection: The absorbance was measured on an Envision plate reader.

Figure 15:
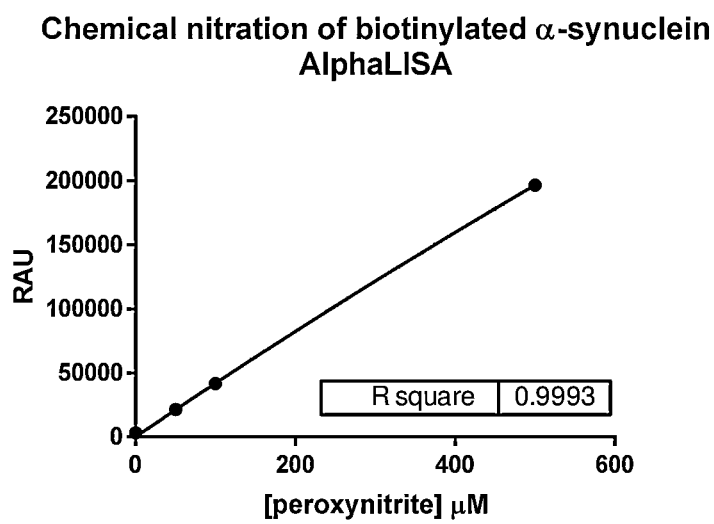
FIG. 15 is a graph showing the chemical nitration of biotinylated α-synuclein in AlphaLISA assay plotted against the concentration of peroxynitrite.

Results: The absorbance of nitrated α-synuclein from the chemical nitration conditions using SEQ ID NO: 4 were plotted against the concentration of the peroxynitrite (see FIG. 15). The level of nitrated α-synuclein increased linearly as the concentration of the peroxynitrite increased.

Figure 16:
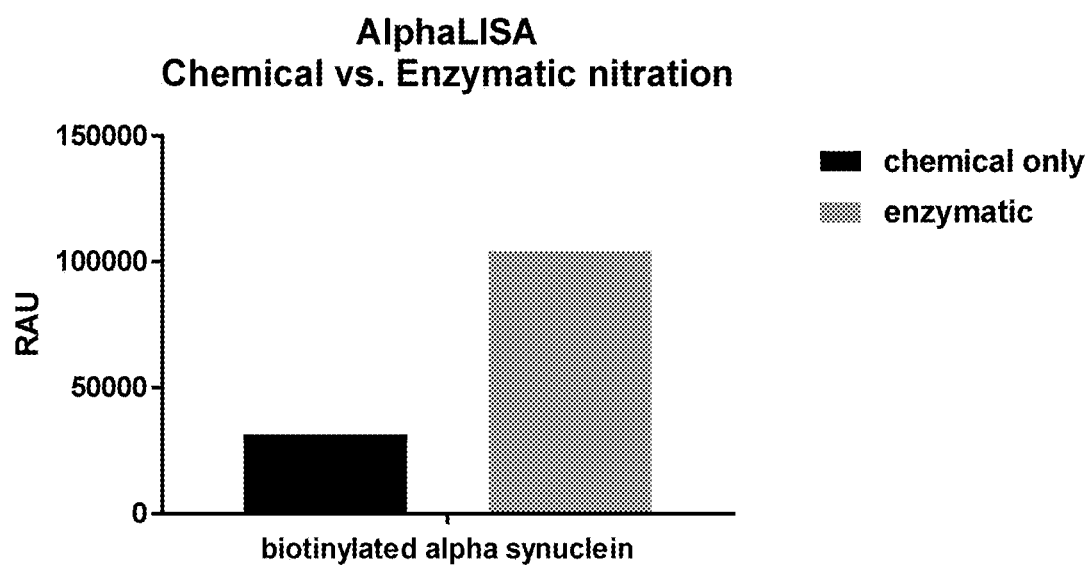
FIG. 16 is a graph showing optical density of nitrated α-synuclein in chemical and enzymatic one-pot nitration conditions of α-synuclein Biotinylated Peptide 7 with peroxynitrite in an AlphaLISA assay.

The absorbance of nitrated α-synuclein from enzymatic nitration using SEQ ID NO: 4 is shown in FIG. 16. The level of nitrated α-synuclein from enzymatic nitration was about 4× the level of nitrated α-synuclein from chemical nitration. This data supports that nitration of α-synuclein is enzyme-dependent.

Example 10—Nitration of α-Synuclein Biotinylated Peptide: Sandwich ELISA

The following example demonstrates the nitration of α-synuclein with and without the Q FT fractions. A sandwich ELISA protocol was used to detect the level of nitrated α-synuclein.

Materials: The materials and reagents used in this example are as follows:

| Reagent | Vendor | Catalog No. |
|---|---|---|
| α-synuclein, 1.0 mg/mL MDVFMKGLSKAKEGVVAAAEKTKQGVAEAAGKTKEGVLYV GSKTKEGVVHGVATVAEKTKEQVTNVGGAVVTGVTAVAQK TVEGAGSIAAATGFVKKDQLGKNEEGAPQEGILEDMPVDP DNEAYEMPSEEGYQDYEPEA (SEQ ID NO: 3) | rPeptides | S-1001-2 |
| Peroxynitrite | EMD Millipore | 20-107 |
| NaOH, 10.0N | Spectrum | S-395 |
| Tris, pH 8.8, 1.0M | Biovision | 2107-100 |
| Q Flow through of rat brain | Rockland | RT-T077 |
| High-binding ELISA plates | CoStar | 3590 |
| 10x Casein | Vector Labs | SP-5020 |
| Anti-nitro-α/β-Synuclein Antibody, clone nSyn12 | EMD Millipore | 36-011 |
| Biotinylated anti-SNCA mAb 6H7 | Imago | 6H7 |
| Avidin D-HRP | Vector Labs | A-2004 |
| 10X TBS | BioBasic | A0027 |
| TMB substrate | EMD Millipore | CL07-100ML |
| 10.0N sulfuric acid | Millipore | 1.60315.1000 |

Methods:

Preparation of Reagents: A 110 mM stock solution of peroxynitrite (ONOO⁻) was diluted so that a final concentration in reactions of 100 μM was generated by by adding 1.5 μL to 80 μL of 0.3 M NaOH; 500 μM by adding 2.47 μL to 24.70 μL of 0.3 M NaOH; and 1000 μM by adding 4.94 μL to 22.23 μL of 0.3 M NaOH.

A 1.0 μg/mL solution of biotinylated 6H7 secondary antibody was prepared as follows: 1.35 μL of 1.48 mg/mL stock solution of biotinylated anti-SNCA mAb 6H7 to 1999 mL of Assay Buffer.

A 1/2500× dilution solution of AvidinD-HRP solution was prepare as follows: 2 μL of the stock solution of the Avidin D-HRP was added to 5 mL of the Assay Buffer.

ELISA Plate: First, an ELISA plate was coated with 100 μL/well of 1.0 μg/mL of nSyn12 antibody (1/1000×). The plate was then sealed and stored overnight at 4° C.

Nitration Reaction Conditions: The following nitration reactions (20 μL) were set up in the small round bottom plate:

| Condition | Plate Wells | α-synuclein 3.6 mM (μL) | ONOO⁻ or NaOH (μL) | [ONOO⁻] (μM) | 100 mM Tris-HCl, pH 8.8 (μL) | Q FT 4 mg/mL (μL) |
|---|---|---|---|---|---|---|
| 1 | A1-B1 | 1 | 1 | 0 | 18 | 0 |
| 2 | C1-D1 | 1 | 1 | 100 | 18 | 0 |
| 3 | E1-F1 | 1 | 1 | 500 | 18 | 0 |

| Condition | Plate Wells | α-synuclein 3.6 mM (μL) | ONOO⁻ or NaOH (μL) | [ONOO⁻] (μM) | 100 mM Tris-HCl, pH 8.8 (μL) | Q FT 4 mg/mL (μL) |
|---|---|---|---|---|---|---|
| 4 | G1-H1 | 1 | 1 | 1000 | 18 | 0 |
| 5 | A2-B2 | 1 | 1 | 100 | 17 | 1 |
| 6 | C2-D2 | 1 | 1 | 100 | 16.5 | 1.5 |
| 7 | E2-F2 | 1 | 1 | 100 | 16 | 2 |
| 8 | G2-H2 | 1 | 1 | 100 | 15.5 | 2.5 |

Nitration reactions (20 μL) were set up in the small round bottom plate as follows: α-synuclein (SEQ ID NO: 3), Tris buffer, and Q FT were added to the wells and mixed. The plate was then sealed and placed in a 37° C. water bath for 5 minutes. The plate was then removed from the bath and placed into a Styrofoam box filled with 1 inch of 37° C. water. The seal was removed and the peroxynitrite was quickly added to the corresponding wells. The plate was immediately sealed, lightly tapped to mix the reagents, and placed back in the 37° C. water bath. The plate was lightly tapped every 30 seconds for the first 4 minutes and then every minute until 10 minutes had elapsed. The plate was then removed from the water bath.

Then 4 μL of the reaction was added to 196 μL of 0.1% casein/TBS buffer ("Assay Buffer") in a new round bottom assay plate. The reagents were mixed well. The plate was then sealed and stored at −20° C. overnight. The coating solution was then removed from the ELISA plate by inverting and tapping the plate dry. The plate was then blocked with 300 μL/well of 3% casein/TBS (diluted from 10% casein stock solution) for 1.5 hours at room temperature. The blocking solution was then removed, and the plate was washed 2× with 300 μL/well of 1×TBS with 0.05% TWEEN®-20 (TBST). Then 100 μL of the diluted reaction samples were added to the corresponding wells of the ELISA plate. Subsequently the plate was sealed and incubated for 2 hours at room temperature on a plate shaker at 400 rpm.

Subsequently, 100 μL of the biotinylated 6H7 mAb solution was added to each well. The plate was then sealed and incubated for 1 hour at room temperature on a plate shaker at 400 rpm. The solution was removed from the ELISA plate by inverting and tapping the plate. The plate was then washed 5× with 300 μL/well TBST.

Detection: Next, 100 μL of the Avidin-HRP solution was added to each well, and the plate was sealed and incubated for 30 minutes at room temperature on a plate shaker at 400 rpm. The solution was then removed from the ELISA plate by inverting and tapping the plate. Next, the plate was washed 5× with 300 μL/well TBST.

Finally, 50 μL of TMB solution was added to each well. The blue color was developed for 5 to 10 minutes, at which point 50 μL of the stop solution (1.0 N sulfuric acid) was added to each well. The absorbance was recorded on a plate reader set at 450 nm with 620 nm subtraction.

Figure 17:
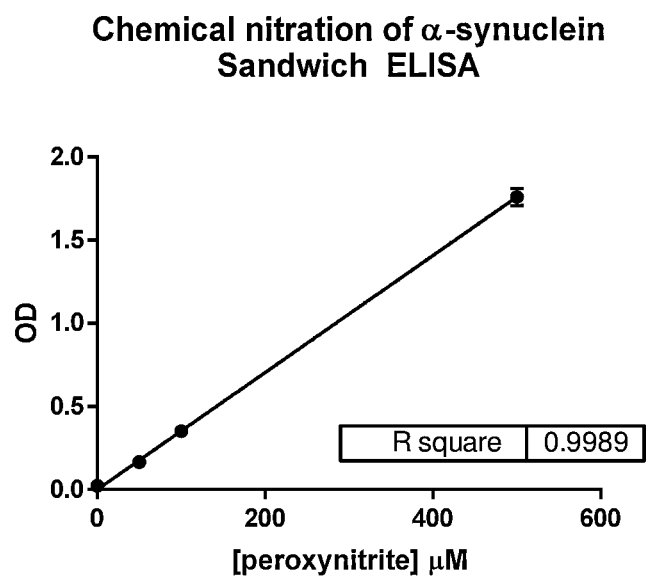
FIG. 17 is a graph showing the chemical nitration of biotinylated α-synuclein in Sandwich ELISA assay plotted against the concentration of peroxynitrite.

Results: The optical density of nitrated α-synuclein from the chemical nitration conditions using SEQ ID NO: 4 were plotted against the concentration of the peroxynitrite (FIG. 17). The optical density increased linearly as the concentration of peroxynitrite increased.

Figure 18:
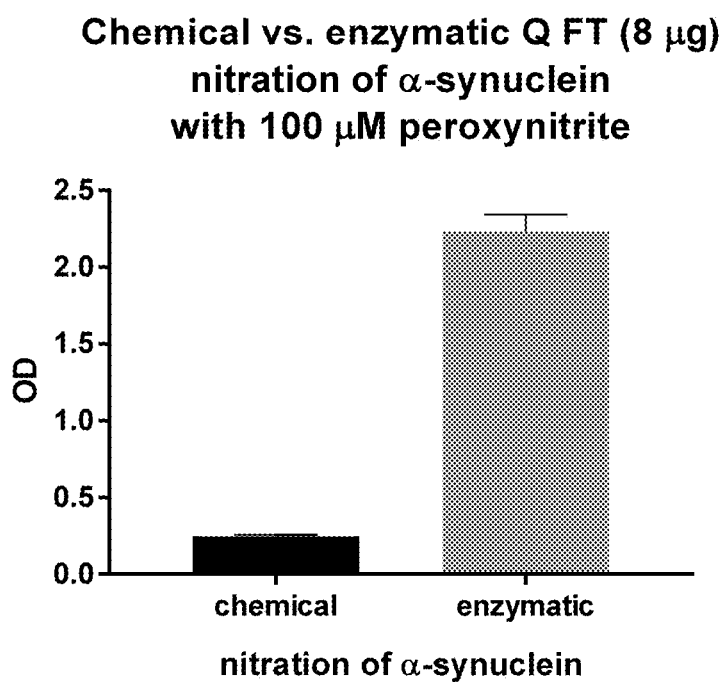
FIG. 18 is a graph showing optical density of nitrated α-synuclein in chemical and enzymatic one-pot nitration conditions of α-synuclein Biotinylated Peptide 7 with peroxynitrite in an ELISA assay.

The optical densities of nitrated α-synuclein from the chemical nitration with 100 μM peroxynitrite and the enzymatic (8 μg of Q FT) nitration with 100 μM peroxynitrite, using SEQ ID NO: 4, are shown in FIG. 18. The optical density of nitrated α-synuclein from the enzymatic nitration was almost 10× the optical density of nitrated α-synuclein from the chemical nitration. This data supports that nitration of α-synuclein is enzyme-dependent.

Example 11—Thermal Shift and Nitrase Activity

The following example measures the activity of nitrase (nitration enzyme) at 0° C., 70° C., 80° C., 90° C., and 99° C. Synuclein nitrase loses activity after heating to 90° C. and eliminated at 99° C.

Methods: The Q SEPHAROSE® flow through (Q FT) fraction was concentrated on an AMICON® Ultra-15 10K filter unit (Millipore UFC901008). Water was added to the Eppendorf® Thermo Mixer (Eppendorf® Catalog No. 5355), and the mixture was heated to 70° C., 80° C., 90° C., or 99° C. Once 1.5 mL microcentrifuge tubes were equilibrated to the desired temperature in wells for 3 minutes, 100 μL of the concentrated Q FT was added to each tube. The lids were closed, and the tubes were heated for 10 minutes. Next, the tubes were removed from the heating wells and placed on ice. Then the tubes were centrifuged at 15,000K for 20 minutes. The supernatant was collected (avoid pellet) and spun again at 15,000K for 20 minutes. Finally, the supernatant was collected, and the Synuclein nitrase activity was measured by the one-pot synuclein nitration assay (Example 8).

Figure 19:
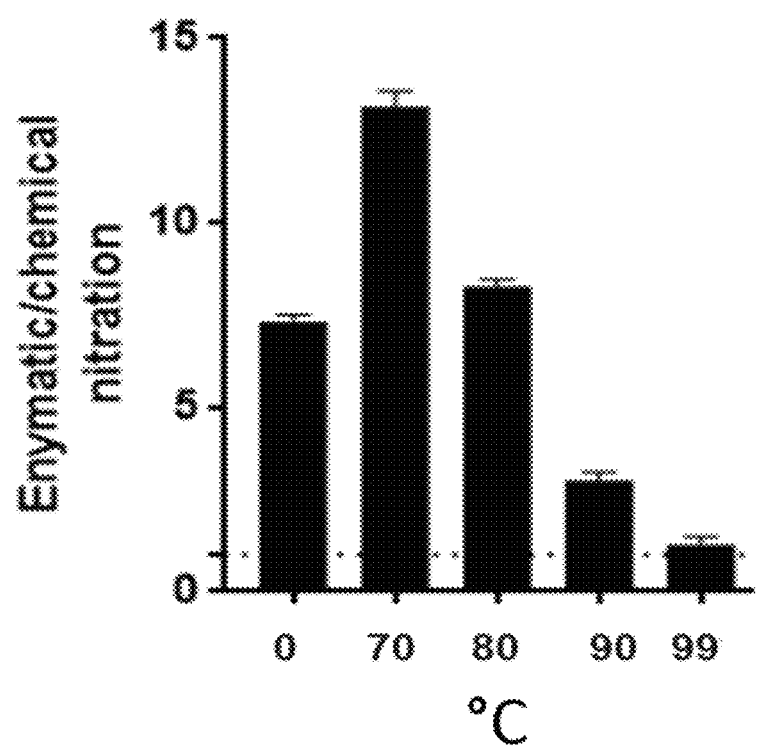
FIG. 19 is a graph showing the enzymatic nitration at different temperatures (thermal shift assay).

Results: Synuclein nitrase activity in the Q FT is stable after heating to 70° C. for 10 minutes with progressive loss of activity at 80° C. and 90° C. There is no activity after heating the Q FT to 99° C. (FIG. 19).

Example 12—Purification: Anion Exchange

The following example demonstrates that Q FT fractions showed Synuclein nitrase activity while Q eluent fractions showed no Synuclein nitrase activity.

Materials: The anion exchange was conducted on a Q SEPHAROSE® column (HiTrap Q HP 5 mL column (GE 17-1154-01) or 1 mL FF column (GE 17-5053-01) using AKTA AVANT® 25 (GE 28930842)).

Methods: The lysis buffer was prepared as follows: 50 mM Tris-HCl at pH 7.5 was added to protease/phosphatase inhibitor cocktail (Millipore No. 5872).

Then 10 mL of the Lysis buffer was cooled with ice and added to 2 rat brains in a Glass homogenizer tube on ice. The mixture was incubated for 30 minutes. Subsequently, the brains were slowly ground using a pestle until a homogenous mixture was achieved while avoiding bubble formation. Then 1.0 mL of the homogenate was added to chilled microfuge tubes and spun at 15,000K for 20 minutes. The supernatant was transferred to new microfuge tubes and spun at 15,000K for 20 minutes. The supernatant was then collected into a 15 mL tube. The tube was sealed and inverted to mix.

The level of protein in cytosolic extract was quantified using an Eppendorf® Spectrometer at A280 and protein separated on anion exchange using the protocol for Q SEPHAROSE® as suggested by the AKTA AVANT® 25 manufacturer for the AKTA Unicorn 6.3 software (GE 29046918). The cytosol was diluted to 5 mg/mL with lysis buffer, and the Q SEPHAROSE® column equilibrated with 10 column volumes of 50 mM lysis buffer (Tris-HCl (pH 7.5) and Protease/Phosphatase Inhibitor Cocktail). The cytosolic extract was loaded directly onto the column using sample pump. The flow through was collected in fractions into 96 deep-well sample plate using fraction collector (2 mL per fraction). The proteins bound on the Q SEPHAR- OSE® column were removed with the lysis buffer and 1 M NaCl solution. The concentration of protein in the flow through and eluent were quantified by the Eppendorf® Spectrometer at $A_{280}$.

The Synuclein nitrase activity in the Q SEPHAROSE® flow through (Q FT) fractions and Q SEPHAROSE® eluent (1 M NaCl eluted fractions) were measured.

Figure 20:
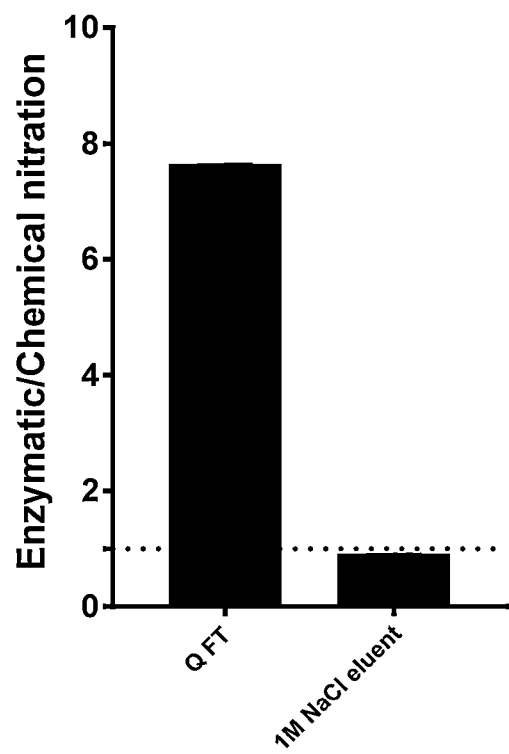
FIG. 20 is a graph showing the enzymatic nitration of the Q SEPHAROSE® Flow Through (Q FT) fractions versus the 1 M NaCl eluent fractions in an anionic exchange purification.

Results: Synuclein nitrase activity was detected in the Q FT fractions, but not in the Q eluent. In fact, measurement of nitration activity showed that Q FT has an 8-fold activity over chemical nitration whereas 1 M NaCl Q eluent fractions displayed similar nitration activity as the chemical nitration conditions (FIG. 20).

Example 13—Purification: Cation Exchange

The following example demonstrates that SP SEPHAROSE® eluted fractions showed synuclein nitrase activity while SP flow through fractions showed no synuclein nitrase activity.

Materials: The cation exchange was conducted on a SP SEPHAROSE® Column (HiTrap SP SEPHAROSE® Column (GE 17515701) or HiScreen SP SEPHAROSE® Column (GE 28950513)) using the ion exchange protocol for Cation exchange SP SEPHAROSE® Column as suggested by AKTA AVANT® 25 for the AKTA's Unicorn 6.3 software (GE 29046918). The flow rate was adjusted to 1 mL/min for a 5 mL column and to 0.5 mL/min for a 1 mL column during sample application, column wash, and elution phase.

Methods: A 50 mM sodium acetate buffer (pH 6.0) was prepared. The thermal shift sample was diluted to 5 mL in 50 mM sodium acetate buffer (pH 6.0). The sample was then filtered with 0.45 µm syringe filter.

The SP SEPHAROSE® column was equilibrated with 5 column volumes of 50 mM sodium acetate buffer (pH 6.0). The filtered sample was loaded into the 5 mL sample loop of the SP SEPHAROSE® column. The flow was collected through fractions into 96 deep-well sample plate using fraction collector (1 mL per fraction). The column was then washed with 5 column volumes of the 50 mM sodium acetate buffer (pH 6.0), and the samples were collected in a 96 deep-well sample plate using fraction collector (1.5-2/0 mL per fraction). The proteins bound on the SP SEPHAROSE® Column were eluted with a linear elution gradient starting with 50 mM sodium acetate buffer (pH 6.0) and ramping up linearly to 50 mM sodium acetate buffer (pH 6.0) with 1 M NaCl. The eluent fractions were collected into a 96 deep-well sample plate using fraction collector (1-1.5 mL per fraction).

The Synuclein nitrase activity in the SP SEPHAROSE® flow through fractions and SP SEPHAROSE® eluent (1 M NaCl eluted fractions) were measured.

Figure 21:
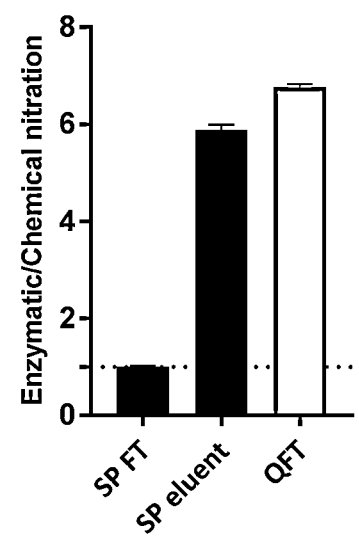
FIG. 21 is a graph showing the enzymatic nitration of the SP FT fractions versus the SP eluent fractions versus the Q FT fractions in a cationic exchange purification.

Results: There was Synuclein nitrase activity in the SP eluate fractions, but no activity in the SP flow through fractions. (FIG. 21).

Example 14—Purification: Size Exclusion Chromatography

The following example demonstrates where synuclein nitrase activity elutes off of SUPERDEX® 75 size exclusion chromatography.

Materials: Size exclusion chromatography was conducted on a SUPERDEX® 75 10/300 GL Column (GE 29148721) using the size exclusion chromatography protocol suggested by AKTA AVANT® 25 manufacturer (GE Life Sciences) for AKTA's Unicorn 6.3 software (GE 29046918). The flow rate was adjusted to 0.5 mL/min.

Methods: A 100 mM Tris plus 1 M EDTA exchange buffer was prepared. The thermal shift sample in Example 4 was diluted with the exchange buffer, and the sample was then filtered through a 0.45 µm syringe filter.

The SUPERDEX® column was equilibrated with 50 mL of water and then with 50 mL of the exchange buffer. Then 300 µL of the filtered sample was inject into the 1 mL sample loop (an empty loop with 1 mL of buffer) and eluted fractions collected.

The synuclein nitrase activity in the size exclusion chromatography (SEC) fractions was measured.

Figure 22:
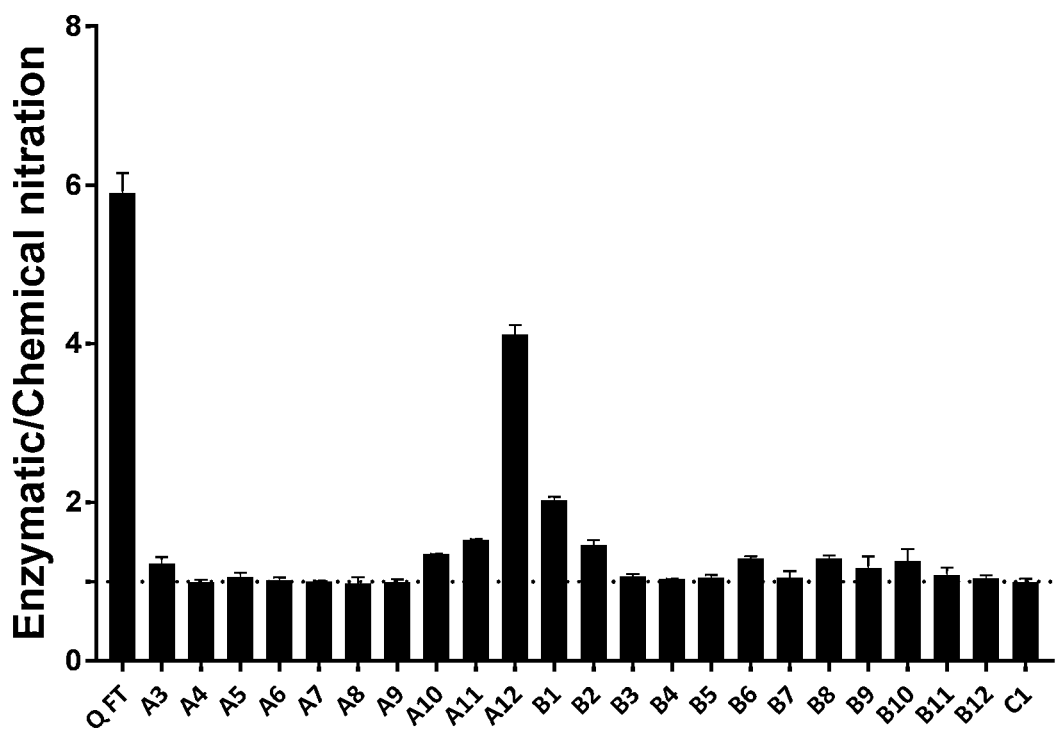
FIG. 22 is a graph showing the enzymatic nitration of discreet molecular weight fractions.
Figure 23:
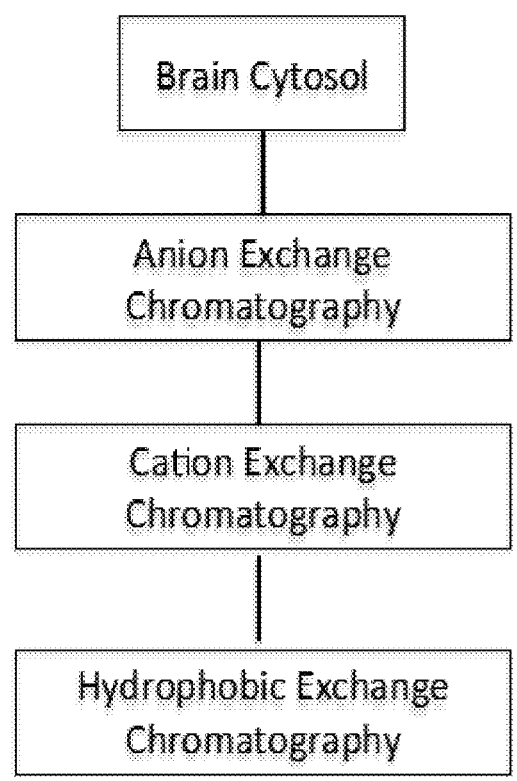
FIG. 23 is a flow chart demonstrating a purification procedure of α-synuclein nitration enzyme including anion exchange, cation exchange, and hydrophobic exchange chromatography.

Results: The synuclein nitrase activity was in discreet molecular weight fraction with trace of activity present in adjacent fractions of higher and lower molecular weight of gel filtration SEC (FIG. 22).

Example 15—Inhibition of Synuclein Nitrase Activity with a Tool Compound

This example demonstrates that a compound, e.g., a small molecule inhibits synuclein nitrase activity via, e.g., inhibiting α-synuclein nitration enzyme.

Background: A compound that looks like peroxynitrite or other nitrating agents, e.g., tetranitromethane might be able to bind in the active site of the α-synuclein nitration enzyme and thereby inhibit peroxynitrite from binding and enabling the catalysis of α-synuclein nitration. Therefore, a number of compounds with these properties were screened.

Validation of activity against the enzyme itself can be conducted using negative controls such as chemical nitration (peroxynitrite only) of α-synuclein. Viable hits for advancing into structure activity relationships (SAR) will specifically inhibit, in a dose responsive manner, the protein-dependent, synuclein nitration activity at a concentration of, e.g., <10 µM and have chemical properties consistent with hit expansion possibilities.

Methods: See Example 2, FIG. 4 for assay conditions and Example 7, FIG. 9 for ELISA conditions, except use 1 µg/mL of nitrosynuclein antibody nSy12 (Millipore #36-011) to coat the plate and biotinylated anti-synuclein antibody 6H7 (Imago Pharmaceuticals) for detection.

This data provided proof-of-concept that the α-synuclein nitration enzyme can be inhibited by a small molecule inhibitor and, together with literature data showing the deleterious effect of α-synuclein nitration in PD models, suggests that inhibiting this enzyme could be a viable disease-modifying approach for PD. NB001, however, may not be a viable starting point for hit expansion activities.

Figure 12:
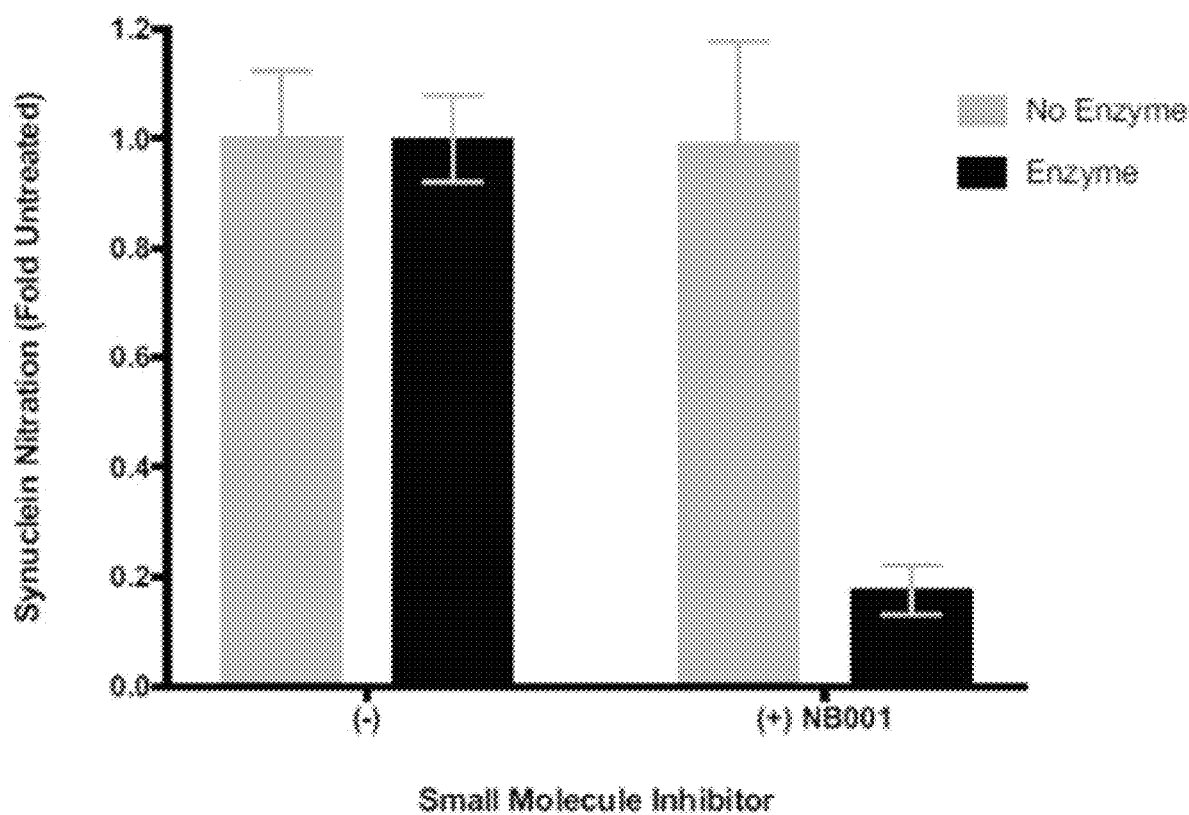
FIG. 12 is a graph showing that nitromethane inhibits enzyme, but not chemical, mediated nitration.

Results: Of the screened compounds, 10 µM nitromethane, a structural analog of tetranitromethane, inhibited only the enzyme mediated α-synuclein nitration and not the chemical nitration (FIG. 12).

OTHER EMBODIMENTS

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure that come within known or customary practice within the art to which the disclosure pertains and may be applied to the essential features hereinbefore set forth, and follows in the scope of the claims. Other embodiments are within the claims.

What is claimed is:

1. A method of identifying a compound that inhibits a nitration enzyme, said method comprising:
   (a) providing a first composition comprising an α-synuclein, peroxynitrite, and the nitration enzyme;
   (b) providing a second composition by contacting a compound with said first composition; and
   (c) measuring the level of nitrated α-synuclein in the second composition, wherein a reduction in the level of nitrated α-synuclein in the second composition compared to the first composition indicates that the compound inhibits the nitration enzyme, and wherein the nitration enzyme is an α-synuclein nitration enzyme.

2. The method of claim 1, wherein the α-synuclein contains tyrosine nitrated by synuclein nitrase or any one of SEQ ID NOS: 1-4.

3. The method of claim 1, wherein measuring the level of nitrated α-synuclein comprises:
   (i) contacting the second composition with a nitrated α-synuclein antibody or a nitrotyrosine antibody; and
   (ii) measuring the optical density of the level of nitrated α-synuclein.

4. The method of claim 1, wherein said compound comprises a nitromethane moiety.

5. The method of claim 1, wherein said compound comprises a peroxynitrite moiety.

6. A method of inhibiting α-synuclein nitration enzyme in a subject in need thereof, said method comprising administering to the subject a compound identified using the method of claim 1.

7. The method of claim 6, wherein the subject in need thereof suffers from a neurodegenerative disease.

8. The method of claim 7, wherein the neurodegenerative disease comprises Parkinson's disease, amyotrophic lateral sclerosis, Alzheimer's disease, or Huntington's disease.

9. The method of claim 6, wherein the compound comprises a peroxynitrite moiety.

10. The method of claim 6, wherein the compound comprises a nitromethane moiety.

* * * * *

```
                         SEQUENCE LISTING

<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Biotinylated

<400> SEQUENCE: 1

Glu Glu Gly Tyr Gln Asp Tyr Glu Pro Glu
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Biotinylated

<400> SEQUENCE: 2

Ser Glu Glu Gly Tyr Gln Asp Tyr Glu Pro Glu Ala
1               5                   10

<210> SEQ ID NO 3
<211> LENGTH: 140
<212> TYPE: PRT
<213> ORGANISM: Homo sapiens

<400> SEQUENCE: 3

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 4
<211> LENGTH: 10
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Biotinylated

<400> SEQUENCE: 4

Glu Glu Gly Tyr Gln Asp Tyr Glu Pro Glu
1               5                   10
```